United States Patent
Biswas et al.

(10) Patent No.: US 10,196,413 B2
(45) Date of Patent: Feb. 5, 2019

(54) CHIRAL DIHYDROBENZOAZAPHOSPHOLE LIGANDS AND SYNTHESIS THEREOF

(71) Applicant: Boehringer Ingelheim International GmbH, Ingelheim am Rhein (DE)

(72) Inventors: Soumik Biswas, Danbury, CT (US); Jean-Nicolas Desrosiers, Southbury, CT (US); Kendricks Lao, Coventry, CT (US); Hari P. R. Mangunuru, Danbury, CT (US); Bo Qu, Brookfield, CT (US); Sonia Rodriguez, New Milford, CT (US); Chris Hugh Senanayake, Brookfield, CT (US); Joshua Daniel Sieber, Sandy Hook, CT (US); Xiao-Jun Wang, Ridgefield, CT (US); Nathan K. Yee, Danbury, CT (US); Yongda Zhang, Sandy Hook, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/831,419

(22) Filed: Dec. 5, 2017

(65) Prior Publication Data

US 2018/0155377 A1    Jun. 7, 2018

Related U.S. Application Data

(60) Provisional application No. 62/430,375, filed on Dec. 6, 2016.

(51) Int. Cl.
| | | |
|---|---|---|
| C07F 9/6581 | (2006.01) | |
| C07F 9/6584 | (2006.01) | |
| C07F 15/00 | (2006.01) | |
| C07B 53/00 | (2006.01) | |

(52) U.S. Cl.
CPC .......... *C07F 9/65844* (2013.01); *C07B 53/00* (2013.01); *C07F 9/65811* (2013.01); *C07F 15/0073* (2013.01)

(58) Field of Classification Search
CPC ....................... C07F 9/65844; C07F 9/65811
See application file for complete search history.

(56) References Cited

U.S. PATENT DOCUMENTS

| | | |
|---|---|---|
| 8,552,212 B2 | 10/2013 | Qu et al. |
| 8,946,418 B1 | 2/2015 | Haddad et al. |

FOREIGN PATENT DOCUMENTS

WO    2011056737 A1    5/2011

OTHER PUBLICATIONS

Issleib et al. CAS Accession No. 1971:112130.*
Candice, "Enantioseselective Hydroformylation of Aniline Derivatives", Journal of Organic Chemistry, vol. 26, 2011, p. 7590-7596.
Lightburn, "Catalytic Scaffolding Ligands: An Efficient Strategy for Directing Reactions", Journal of American Chemical Society, vol. 130, 2008, p. 9210-9211.
Worthy, "Regioselective Hydroformylation of Sulfonamides using a Scaffolding Ligand", Organic Letters, vol. 11, 2009, p. 2764-2767.
Aluri, "Excess Aromatic 2 P Ligands: Formation of a Heterocyclic 1,2-Diphosphine by the Addition of a tBuli and Subsequent inverse Addition pf the Product at the P=C Bonds of Two Molecules 1-Neopentyl-1,3-benzazaphosphole", Heteroatom Chemistry, vol. 26, 2015, p. 426-435.
Heinicke, "Ambident Reactivity of P?CH-N-Heterocycles: Lithiation and Substitution Sites", Phosphorus, Sulfur and Silicon and the Related Elements, vol. 186, 2011, p. 683-687.
Aluri, "Sterically and Polarity-Controlled Reactions of TBuli with PCH-NR Heterocycles: Novel Heterocyclic P- and P—O-Ligands and Preliminary Tests in Transition Metal Catalysis", Chemistry A European Journal, vol. 14, 2008, p. 4328-4335.
Ghalib, "Solvent-controlled lithiation of PC—N-heterocycles: Synthesis of mono- and Bis(trimethylsilyl)-tert-butyl-dihydrobenzazaphospholes—A new type of highly bulky and basic phosphine ligands", Journal of Organometallic Chemistrry, 2014, p. 763-764.
International Search Report and Written Opinion for PCT/US2017/064582 dated Feb. 27, 2018.

* cited by examiner

*Primary Examiner* — Joseph R Kosack
(74) *Attorney, Agent, or Firm* — David L. Kershner

(57) ABSTRACT

This invention relates to novel phosphorous ligands useful for organic transformations. Methods of making and using the ligands in organic synthesis are described. The invention also relates to processes for preparing the novel ligands.

10 Claims, No Drawings

CHIRAL DIHYDROBENZOAZAPHOSPHOLE LIGANDS AND SYNTHESIS THEREOF

FIELD OF THE INVENTION

This invention describes novel phosphorous ligands useful in asymmetric transformations in organic synthesis and novel processes for their preparation.

BACKGROUND

The increasing demand to produce enantiomerically pure pharmaceuticals, agrochemicals, flavors, and other fine chemicals has advanced the field of asymmetric catalytic technologies. Development of efficient asymmetric metal-catalyzed transformations has played a central role for the advancement of asymmetric catalysis. In the past decades, metal-catalyzed reactions with chiral phosphine ligands have been widely utilized and advanced for variety of asymmetric transformations. Development of efficient chiral phosphorus ligands is essential for the success of asymmetric hydrogenation. Known chiral phosphorus ligands in this field include Knowles' DIPAMP [Knowles, W. S. *Acc. Chem. Res.* 1983, 16, 106], Kagan's DIOP [Kagan et al, *J. Am. Chem. Soc.* 1972, 94, 6429], Noyori's BINAP [Noyori, R. *Chem. Soc. Rev.* 1989, 18, 187], Burk's Duphos and BPE [Burk, M. J. et al, Organometallics 1990, 9, 2653; Burk, M. J. et al, *Angew. Chem., Int. Ed. Engl.* 1990, 29, 1462], Imamoto's BisP* [Imamoto, T. et al, J. Am. Chem. Soc. 1997, 119, 1799], Zhang's PennPhos [Zhang, X. et al, *Angew. Chem. Int. Ed. Engl.* 1999, 38, 516] and TangPhos [US2004/0229846 and Zhang, X. et al, *Angew. Chem. Int. Ed.* 2002, 41, 1613.], Pfizer's trichickenfootphos [WO2005/087370 and Hoge, G. et al, *J. Am. Chem. Soc.* 2004, 126, 5966].

More recently, families of phosphine ligands ontaining a unique dihydrobenzooxaphosphole (BOP) core which are structurally rigid, electronically and sterically tunable, and air-stable have been discovered. For example, one family of ligands (U.S. Pat. No. 9,096,626) is represented by formulas (A) and (B).

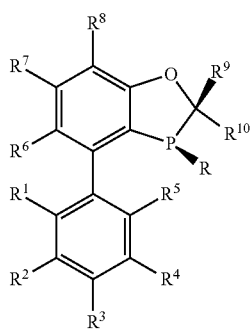

A

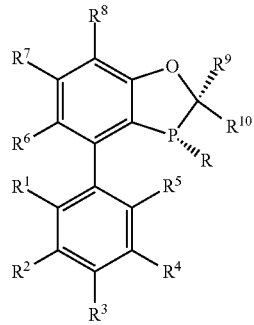

B

Another family of BOP ligands (U.S. Pat. No. 8,552,212) is represented by formulas C and D.

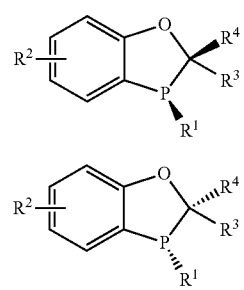

C

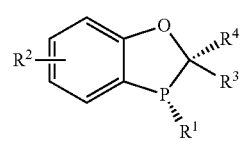

D

Another family of ligands (U.S. Pat. No. 8,946,418) is represented by formulas E and F.

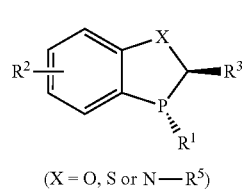

E (X = O, S or N—$R^5$)

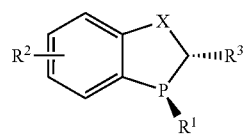

F

These unique chiral BOP ligands have demonstrated superior reactivity and selectivity for various organic and asymmetric transformations including Suzuki-Miyaura cross-coupling reaction, Negishi coupling, asymmetric hydrogenation of enamides, ketones, and unfunctionalized alkenes, asymmetric proprogylation, asymmetric ketone and imine addition, asymmetric dearomative cyclization and reductive alkynone cyclization, asymmetric hydroboration and asymmetric ring-opening reactions.

Although tremendous progress has been made in the field of asymmetric hydrogenation and many efficient chiral ligands have been developed, the design of new efficient ligands continues to be important since there is no universal ligand for hydrogenation of various kinds of prochiral substrates.

BRIEF SUMMARY OF THE INVENTION

This invention relates to novel phosphorous ligands of general formulas I and II. Methods of using the ligands in organic synthesis are described. The invention also relates to a process of preparing the novel ligands.

DETAILED DESCRIPTION OF THE INVENTION

One embodiment of the present invention is directed to a novel class of phosphorous ligands represented by formula I

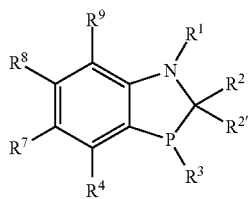

wherein each $R^1$ is selected from H, $C_{1-6}$alkyl, —C(O)$C_{1-6}$alkyl, —C(O)NH$R^5$, —SO$_2$C$_{1-6}$alkyl, —S(O)C$_{1-6}$alkyl, —P(O)$R^{13}R^{14}$, —Si$R^{13}$, —C(=N$R^{13}$)N$R^{13}R^{14}$, optionally substituted benzyl and optionally substituted aryl or heteroaryl;

$R^2$ and $R^{2'}$ are each independently selected from the group consisting of hydrogen, halo, perhaloalkyl, —N$R^{11}R^{12}$, —O$R^{11}$, —S$R^{11}$, —Si($R^{11}$)$_3$, P(O)$R^{13}R^{14}$, —CN, —NO$_2$, —OH, alkyl, alkenyl, alkynyl, cycloalkyl, heterocycloalkyl, arylalkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted, or where adjacent $R^2$ and $R^{2'}$ and $R^9$ and $R^{9'}$ taken together with the carbon atoms to which they are bound to form a substituted or unsubstituted cycloalkyl ring;

$R^3$ is selected from alkyl, cycloalkyl or optionally substituted aryl;

$R^4$ is hydrogen, halo, perhaloalkyl, —N$R^{11}R^{12}$, —O$R^{11}$, —S$R^{11}$, —Si($R^{11}$)$_3$, —CN, —NO$_2$, —OH, alkyl, alkenyl, alkynyl, cycloalkyl, heterocycloalkyl, benzyl, aryl, alkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, aryl and heteroaryl are unsubstituted or substituted; or $R^4$ is —X—$R^6$; or —$R^4$ is the group

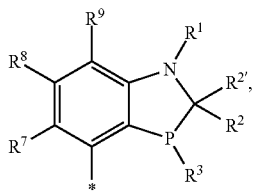

wherein * indicates the point of attachment;
X is selected from O, N$R^{10}$, C$R^{11}R^{12}$ and S;
$R^5$ is selected from $C_{1-6}$ alkyl and optionally substituted phenyl each $R^6$, $R^7$, $R^8$ and $R^9$ is independently selected from the group consisting of hydrogen, halo, perhaloalkyl, —N$R^{11}R^{12}$, —O$R^{11}$, —S$R^{11}$, —Si($R^{11}$)$_3$, —CN, —NO$_2$, —OH, alkyl, alkenyl, alkynyl, cycloalkyl, heterocycloalkyl, benzyl, aryl, alkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, aryl and heteroaryl are unsubstituted or substituted;

$R^{10}$, $R^{11}$ and $R^{12}$ are independently selected from H, $C_{1-6}$alkyl, $C_{1-6}$alkenyl, $C_{1-6}$alkynyl, perhalo$C_{1-6}$alkyl, —C(O)$C_{1-6}$alkyl, cycloalkyl, heterocyclyl, optionally substituted benzyl, optionally substituted aryl and optionally substituted heteroaryl; and $R^{13}$ and $R^{14}$ are independently selected from $C_{1-6}$alkyl and optionally substituted aryl;

and the diastereomers and enantiomers thereof.

Another embodiment of the present invention is directed to a novel class of phosphorous ligands represented by formula I as described above, wherein

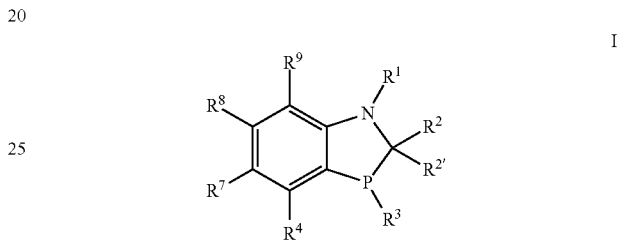

wherein
$R^1$ is selected from H, $C_{1-6}$alkyl, —C(O)$C_{1-6}$alkyl, —C(O)NH$R^5$, —SO$_2$C$_{1-6}$alkyl, optionally substituted benzyl and optionally substituted aryl;

$R^2$ and $R^{2'}$ are independently selected from H, $C_{1-6}$alkyl, $C_{3-6}$cycloalkyl, CH$_2$C$_{3-10}$cycloalkyl, —C(O)C$_{1-6}$alkyl, optionally substituted aryl, heteroaryl or —CH$_2$-aryl and —P(O)$R^8R^9$; or $R^2$ and $R^{2'}$ together with the carbon they are bonded to may form a spiro $C_3$-$C_6$ cycloalkyl ring;

$R^3$ is selected from is selected from $C_{1-6}$alkyl, $C_{3-6}$cycloalkyl and optionally substituted aryl;

$R^4$ is selected from optionally substituted aryl and —X—$R^6$; or $R^4$ is the group

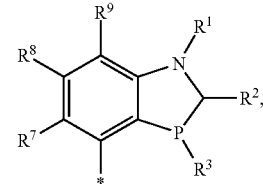

wherein * indicates the point of attachment;
X is selected from a bond, O, —N$R^{10}$ and S;
$R^5$ is selected from $C_{1-6}$alkyl and optionally substituted phenyl
$R^6$ is selected from $C_{1-6}$alkyl, $C_{3-6}$cycloalkyl, optionally substituted aryl and optionally substituted heteroaryl;
$R^7$, $R^8$ and $R^9$ are each H;
$R^{10}$ is selected from H, $C_{1-6}$alkyl, $C_{3-6}$cycloalkyl, optionally substituted aryl and optionally substituted heteroaryl;
$R^{13}$ and $R^{14}$ are independently selected from $C_{1-6}$alkyl and optionally substituted aryl;
and the diastereomers and enantiomers thereof.

In another embodiment there are compounds of formula I as described above, wherein R¹ is selected from H, —C$_{1-3}$alkyl, —C(O)—C$_{1-4}$alkyl, —C(O)NHR⁵, benzyl, and phenyl, optionally substituted with one to two groups selected from —CF₃, —OC$_{1-3}$alkyl, halogen, —NH(C$_{1-3}$alkyl), and —N(C$_{1-3}$alkyl)₂;

R² is selected from H, C$_{1-3}$alkyl, —CH₂-adamantyl, phenyl, pyridyl, -benzyl and —CH₂naphthyl, wherein the phenyl, pyridyl, -benzyl and —CH₂naphthyl is optionally substituted with one to three groups selected from C$_{1-3}$alkyl, —OCH₃—CF₃ and halogen;

R²' is H or if R² is C$_{1-6}$alkyl, R²' may be C$_{1-6}$alkyl; or

R² and R²' together with the carbon they are bonded to may form a spiro cyclopentyl or cyclohexyl ring;

R³ is C$_{1-6}$alkyl;

X is a bond and

R⁴ is selected from phenyl, optionally substituted with one to three groups selected from —OCH₃, —CF, C$_{1-3}$alkyl and halogen; or R⁴ is —X—R⁶; or R⁴ is selected from

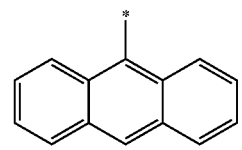 and 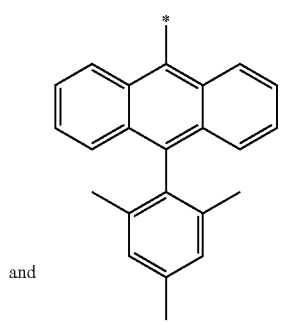 ;

or

R⁴ is the group

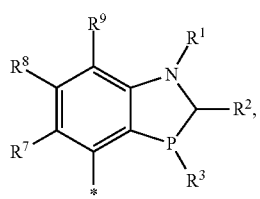

wherein * indicates the point of attachment;
X is O;
R⁵ is phenyl, optionally substituted with one to three groups selected from —OCH₃, —CF, C$_{1-3}$alkyl and halogen;
R⁶ is C$_{1-3}$alkyl; and
R⁷, R⁸ and R⁹ are each H;
and the diastereomers and enantiomers thereof.

In another embodiment there are compounds of formula I as described above, wherein R¹ is selected from H, —CH₃, —C(O)-t-butyl, —C(O)NHR⁵, benzyl, and phenyl, optionally substituted with —CF₃ or —OCH₃;

R² is selected from H, C$_{1-3}$alkyl, —CH₂-adamantyl, 2,4,6-triisopropylbenzyl, —CH₂naphthyl and pyridyl optionally substituted with —OCH₃;

R²' is H or if R² is methyl, R²' may be methyl; or

R² and R²' together with the carbon they are bonded to may form a spiro cyclopentyl or cyclohexyl ring;

R³ is t-butyl;

R⁴ is 2,6-dimethoxyphenyl,

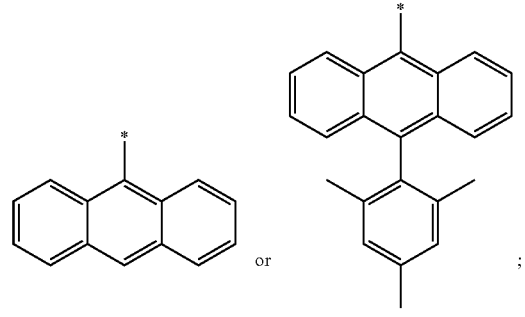

or

R⁴ is the group

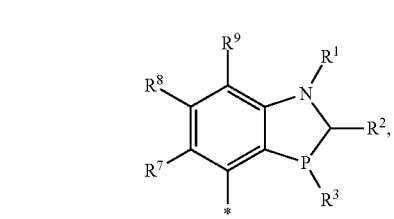

wherein * indicates the point of attachment; or

R⁴ is —X—R⁶;
X is O; and
R⁶ is methyl;
R⁵ is phenyl; and
R⁷, R⁸ and R⁹ are each H;
and the diastereomers and enantiomers thereof.

In another embodiment there is a compound of formula I selected from the group consisting of

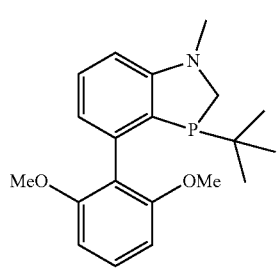

Ia

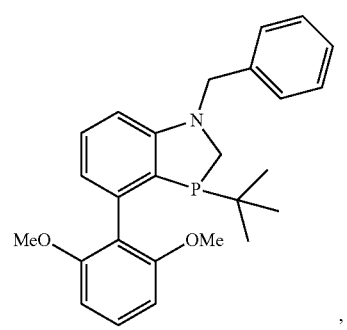

Ib

Ic
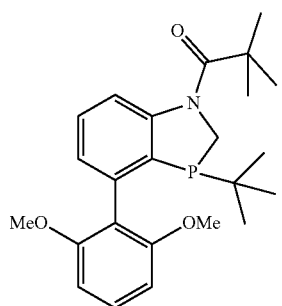
,
Id
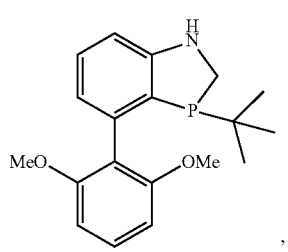
,
Ie
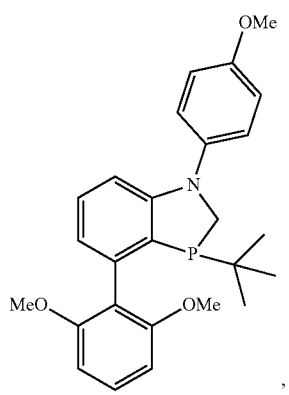
,
If
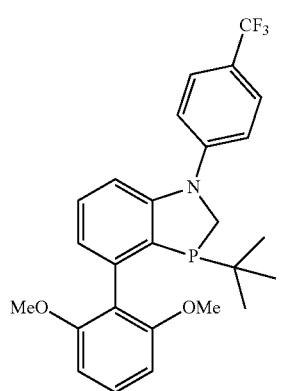
,
Ig
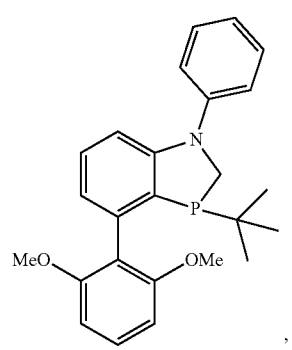
,
Ih
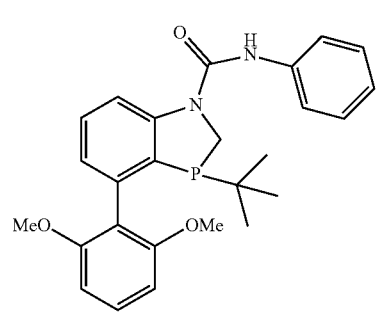
,
Ii
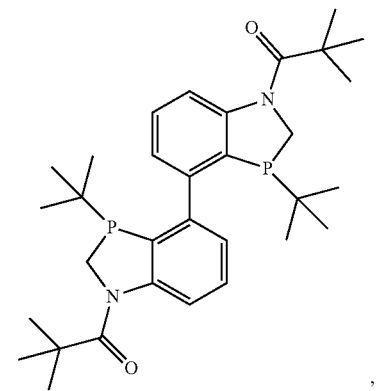
,
Ij
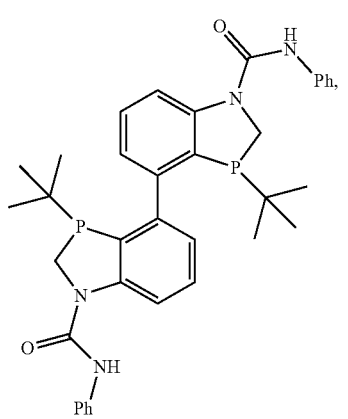

Ik 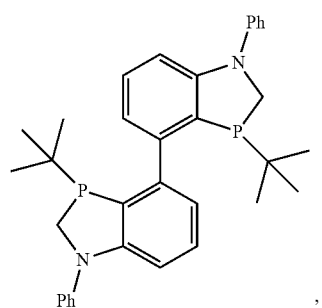,
Il 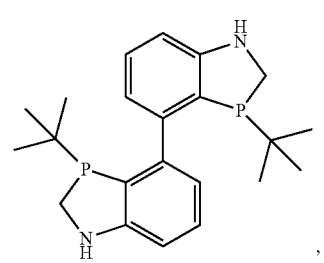,
Im 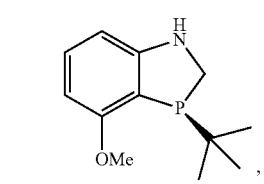,
In 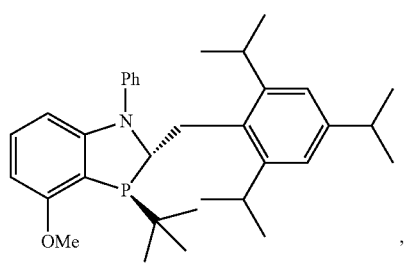,
Io 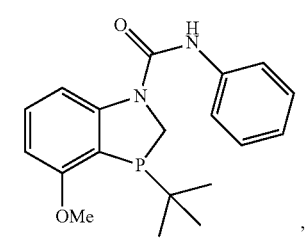,
Ip 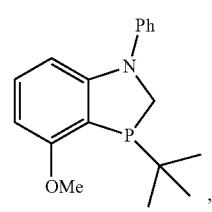,
Iq 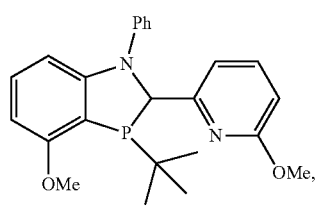,
Ir 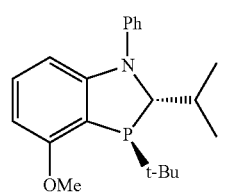,
Is 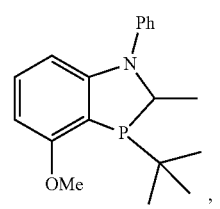,
It 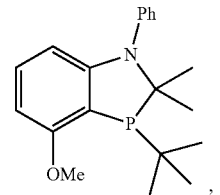,
Iu 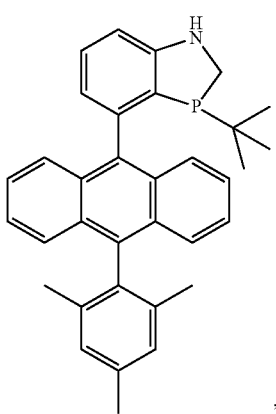, Iv
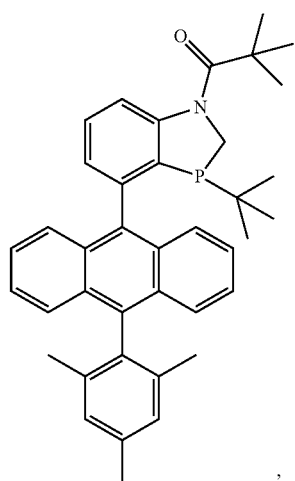
Iw
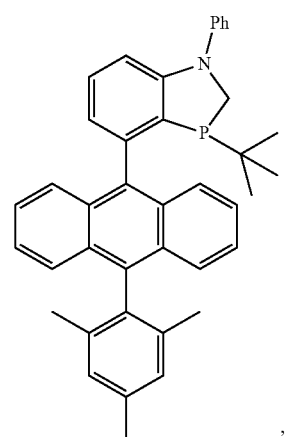
Ix
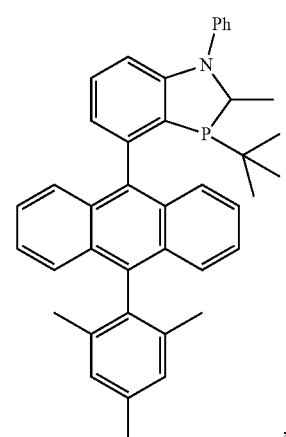
Iy
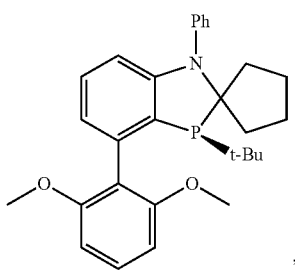
Iz
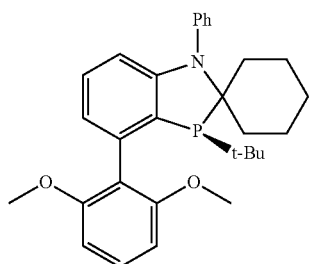
Iaa
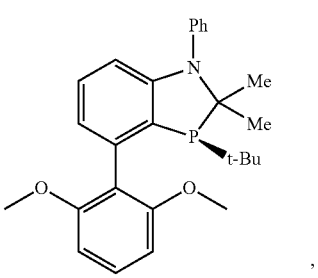
Ibb
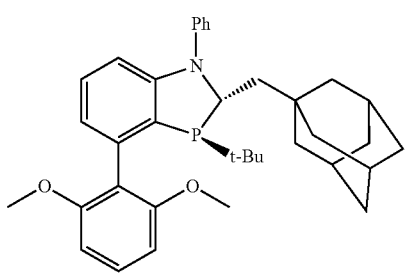
Icc
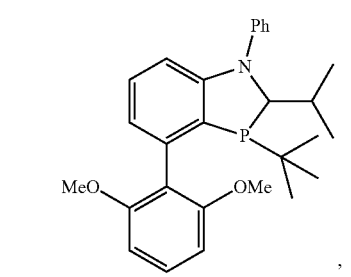
Idd
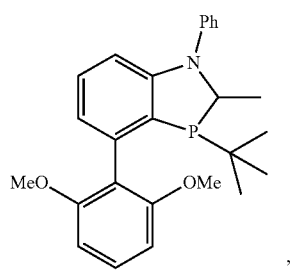

-continued

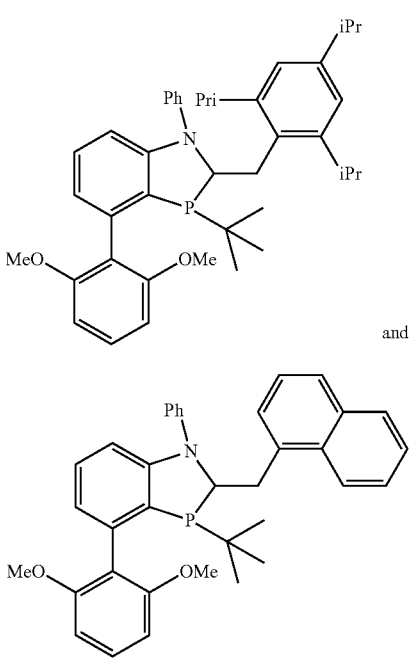

Iee and

Iff and the enantiomers and diastereomers thereof.

The family of ligands represented by formula I have utility in important organic transformations, for example Negishi coupling, Suzuki coupling and asymmetric hydrogenation. Examples are shown in the Synthetic Examples section.

Another embodiment of the invention is directed to compounds of formula II

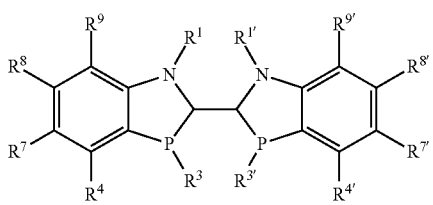

II wherein $R^1$ and $R^{1'}$ are independently selected from H, $C_{1-6}$alkyl, —C(O)$C_{1-6}$alkyl, —C(O)NHR$^5$, —SO$_2$C$_{1-6}$alkyl, —S(O)C$_{1-6}$alkyl, —P(O)R$^{13}$R$^{14}$, —SiR$^{13}$, —C(=NR$^{13}$)NR$^{13}$R$^{14}$, optionally substituted benzyl and optionally substituted aryl or heteroaryl;

$R^3$ and $R^{3'}$ are independently selected from alkyl, cycloalkyl and optionally substituted aryl;

$R^4$, $R^{4'}$, $R^7$, $R^{7'}$, $R^8$, $R^{8'}$, $R^9$ and $R^{9'}$ are independently selected from hydrogen, halo, perhaloalkyl, —NR$^{11}$R$^{12}$, —OR$^{11}$, —SR$^{11}$, —Si(R$^{11}$)$_3$, —CN, —NO$_2$, —OH, alkyl, alkenyl, alkynyl, cycloalkyl, heterocycloalkyl, benzyl, aryl, alkyl, heteroarylalkyl, bicycloaryl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, aryl and heteroaryl are unsubstituted or substituted;

$R^{11}$ and $R^{12}$ are independently selected from H, $C_{1-6}$alkyl, $C_{3-6}$cycloalkyl, CH$_2$C$_{3-10}$cycloalkyl, —C(O)C$_{1-6}$alkyl, optionally substituted aryl, heteroaryl and —CH$_2$-aryl; and $R^{13}$ and $R^{14}$ are independently selected from $C_{1-6}$alkyl and optionally substituted aryl;

and the diastereomers and enantiomers thereof.

In another embodiment there are compounds of formula II as described above, wherein $R^1$ is selected from —SO$_2$aryl, —C(O)-aryl, —C(O)C$_{1-6}$alkyl, —NC(O)-aryl and —NC(O)C$_{1-6}$alkyl, wherein each aryl and alkyl is optionally substituted;

and the diastereomers and enantiomers thereof.

In another embodiment, there is a compound of formula IIa

IIa

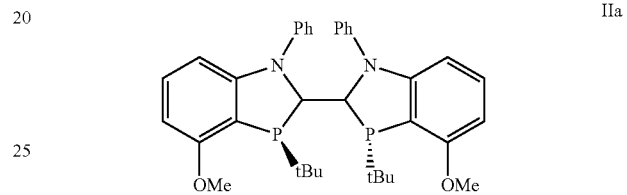

Another embodiment is directed to the synthesis of the core intermediate dihydrobeno[d][1,3]oxaphosphole III comprising

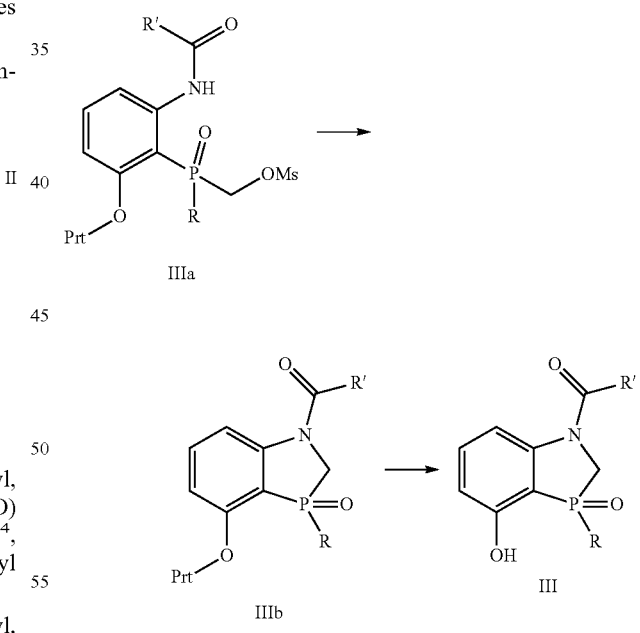

IIIa

IIIb

III

Reacting intermediate IIIa, wherein R' and R are independently selected from $C_{1-6}$alkyl and Prt is a protecting group with a suitable base to provide intermediate IIIb; and Removing the protecting group to provide III.

Another embodiment is directed to the process described above, wherein the intermediate IIIa is prepared by treating intermediate IIIc with methanesulfonyl chloride in the presence of a suitable base

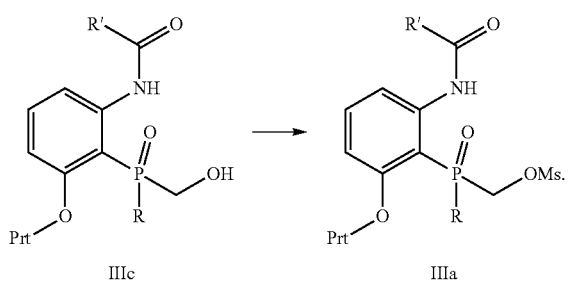

IIIc → IIIa

Another embodiment is directed to the process described in the embodiment above, wherein the intermediate IIIc is prepared by treating intermediate IIId with RPCl$_2$ in the presence of a suitable base followed by treatment with water to form intermediate IIIe followed by treatment with formaldehyde in the presence of a suitable base to provide IIIc

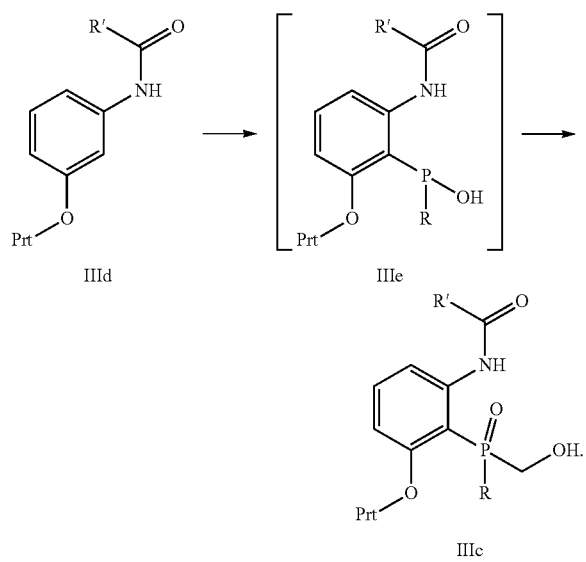

IIId → IIIe → IIIc

Another embodiment is directed to any of the process embodiments above wherein R' and R are both t-butyl and Prt is tetrahydropyranyl.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist.

Some of the compounds of formula (I) can exist in more than one tautomeric form. The invention includes methods for using all such tautomers.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "C$_{1-4}$alkyl" is a saturated aliphatic hydrocarbon monovalent radical containing 1-4 carbons such as methyl, ethyl, n-propyl, 1-methyl-ethyl (isopropyl), n-butyl or t-butyl; "C$_{1-4}$ alkoxy" is a C$_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "C$_{1-n}$-alkyl", wherein n is an integer from 2 to n, either alone or in combination with another radical denotes an acyclic, saturated, branched or linear hydrocarbon radical with 1 to n C atoms. For example the term C$_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "C$_{1-n}$-alkylene" wherein n is an integer 1 to n, either alone or in combination with another radical, denotes an acyclic, straight or branched chain divalent alkyl radical containing from 1 to n carbon atoms. For example the term C$_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "C$_{3-n}$-cycloalkyl", wherein n is an integer 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-azaspiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, non-limiting examples would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —$S(O)_2$—$C_{1-6}$ alkyl, likewise, —S—$R_a$ may be represented as phenyl-S$(O)_m$— when $R_a$ is phenyl and where m is 0, 1 or 2.

As used herein, "optionally substituted" means a group is optionally substituted with one or more groups mentioned in the definitions above or in the embodiments above.

SYNTHETIC EXAMPLES

Example 1: Synthesis of 1-(3-tert-Butyl-4-hydroxy-3-oxo-2,3-dihydro-benzo[1,3]azaphosphol-1-yl)-2,2-dimethyl-propan-1-one (III)

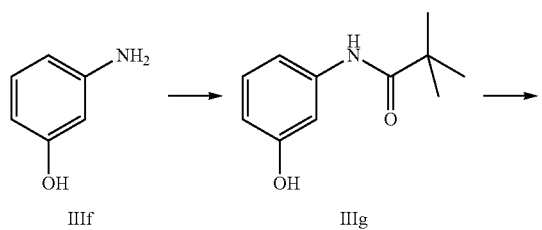

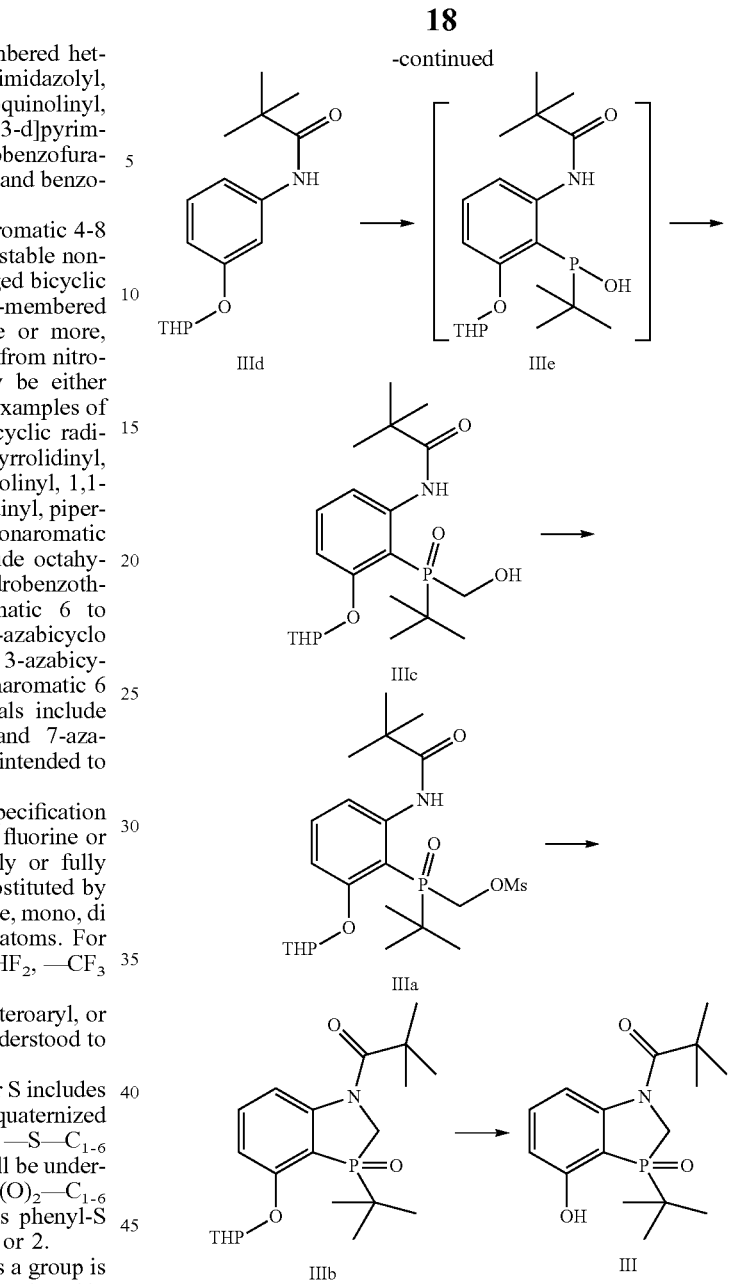

A solution of 3-aminophenol (IIIf) (300 g, 2.75 mol) in THF (2.4 L) was cooled to −10° C. Pivaloyl chloride (339 mL, 2.75 mol) was added while maintaining temperature below −5° C. After complete addition, the mixture was kept for 2 h. Triethylamine (113 mL, 0.825 mol) was added slowly while maintaining temperature below −5° C. and hold for another 2 h. Additional triethylamine (0.1 eq) was added to achieve complete conversion. The reaction mixture was warmed to 23° C. and acidified to pH=1 with conc. HCl. THF was removed by distillation. The solid was collected by filtration and then washed with water to give the product (IIIg) as a white solid (360 g, 68% yield). $^1$H (400 MHz, $CDCl_3$) δ=8.19 (s, 1H), 7.96 (t, J=2.22, 1H), 7.41 (s, 1H), 7.15, (t, J=2.22, 1H), 6.66 (ddd, J=8.16, 2.40, 0.84 Hz, 1H), 6.52 (ddd, J=7.96, 1.98, 0.82 Hz, 1H), 1.34 (s, 9H). $^{13}$C NMR (100 MHz, $CDCl_3$) δ=117.80, 157.77, 138.54, 129.65, 112.03, 110.52, 107.49, 39.82, 27.59.

To a solution of N-(3-hydroxyphenyl)pivalamide (IIIg) (360 g, 1.87 mol) and pyridinium p-toluenesulfonate (PPTS)

(46.87 g, 0.187 mol) in CH$_2$Cl$_2$ (2 L) was added dihydropyran (485 mL, 5.60 mol). The reaction mixture was then heated at 35° C. overnight. Additional dihydropyran (1 eq) was added to push reaction to completion. The reaction was quenched with sat. NaHCO$_3$ (400 mL) and then washed with water twice (400 mL×2). The organic layers were dried with anhydrous MgSO$_4$ and concentrated. The crude product was purified by recrystallization in EtOAc/hexanes to produce the product N-(3-((tetrahydro-2H-pyran-2-yl)oxy)phenyl) pivalamide (Ind) as a white solid (420 g, 81% yield). $^1$H (400 MHz, CDCl$_3$) δ=7.35 (t, J=2.2 Hz, 1H), 7.29 (bs, 1H), 7.21 (t, J=8.1 Hz, 1H), 7.12 (qd, J=0.9, 8.0 Hz, 1H), 6.80 (ddd, J=0.9, 2.5, 8.2, 1H), 5.44 (t, J=3.2, 1H) 3.90 (m, 1H), 3.61 (dtd, J=1.2, 4.1, 11.3 Hz, 1H), 1.99 (m, 1H), 1.84 (m, 2H), 1.55-1.75 (m, 3H), 1.31 (s, 9H). $^{13}$C NMR (100 MHz, CDCl$_3$) δ=176.5, 157.6, 139.1, 129.6, 113.1, 112.4, 108.3, 96.3, 61.9, 39.6, 30.3, 27.6, 25.2, 18.6.

A mixture of IIId (50 g, 180.3 mmol) and THF (500 mL) was cooled to −10° C. under argon. A solution of n-BuLi (181 mL, 453 mmol, 2.5 M in hexanes) was added dropwise maintaining the temperature below 0° C. The mixture was then kept at 2-5° C. for 2 h. A solution of t-BuPCl$_2$ (51.4 g solution, 235 mmol, 72.5% w/w in THF) was added dropwise maintaining the temperature below 0° C. After complete addition, the reaction mixture was warmed up to 23° C. and left overnight at room temperature. Water (50 mL) was added followed by addition of a solution of 6M NaOH solution (60 mL, 360 mmol) and a solution of formaldehyde (2.0 eq., 37 wt % in water). The mixture was heated to remove the organic solvent and reach the internal temperature 70-75° C. Another portion of formaldehyde (3.0 eq.) was added. The mixture was kept at 70-75° C. until the reaction was complete (4 h). The mixture was cooled to 40-45° C. at least over 0.5 h. Methyl t-butyl ether (MTBE) (150 mL) was added. The slurry was further cooled to 20-25° C. at least over 0.5 h. After being stirred at least for 0.5 h at 20-25° C., the solid was collected by filtration and washed with 2V of MTBE (100 mL). The product, N-(2-(tert-butyl(hydroxymethyl)phosphoryl)-3-((tetrahydro-2H-pyran-2-yl)oxy)phenyl)pivalamide (Mc) was dried under vacuum and isolated as a white solid with 40% yield. $^1$H (400 MHz, CDCl$_3$) δ=11.75 (d, J=33.21 Hz, 1H), 8.32 (dd, J=8.44, 3.22 Hz, 1H), 7.42 (t, J=8.42 Hz, 1H), 6.91 (dd, J=8.41, 4.36 Hz, 0.4H, diasteriomer 1), 6.86 (dd, J=8.36, 4.40 Hz, 0.6H, diasteriomer 2), 5.40-5.36 (m, 0.6H, diasteriomer 2), 5.31-5.28 (m, 0.4H, diasteriomer 1), 4.47-4.35, (m, 1.6H), 4.14 (ddd, J=13.77, 3.42, 1.66 Hz, 0.4H, diasteriomer 1), 3.90-3.81 (m, 1H), 3.71-3.60 (m, 1H), 3.33 (ddd, 7.95, 7.01, 4.17 Hz, 0.6H, diasteriomer 2), 3.19 (dt, J=10.04, 1.84 Hz, 0.4H, diasteriomer 1), 2.03-1.62 (m, 6H), 1.32 (s, 9H), 1.21 (m, 9H). $^{13}$C NMR (100 MHz, CDCl$_3$) δ=177.89, 147.12, 146.73, 134.58, 134.41, 115.78, 115.72, 115.58, 115.51, 108.47, 108.41, 108.14, 108.08, 98.85, 97.45, 63.99, 63.46, 59.80, 59.14, 59.05, 58.39, 40.23, 35.94, 35.40, 30.23, 30.13, 27.53, 24.74, 24.64, 24.44, 24.39, 20.18, 19.96. $^{31}$P (162 MHz, CDCl$_3$) δ=59.11, 58.42.

To a solution of Mc (16.39 g, 39.83 mmol) in CH$_2$Cl$_2$ (160 mL) was added TEA (28 mL, 200 mmol). After the solution was cooled to −5° C., MsCl (4.7 mL, 60 mmol) was added dropwise while maintaining the internal temperature below 5° C. After complete addition, the reaction mixture was stirred at room temperature for 1.5 h. The reaction was quenched with water (160 mL) and extracted with CH$_2$Cl$_2$ (32 mL×3). The organic layers were combined, dried with anhydrous MgSO$_4$ and concentrated to remove of most CH$_2$Cl$_2$. Hexane was added and the remained CH$_2$Cl$_2$ was removed. The solid was collected by filtration to give (tert-Butyl(2-pivalamido-6-((tetrahydro-2H-pyran-2-yl) oxy)-phenyl)phosphoryl)methyl methanesulfonate (Ma) as a white solid (18.4 g, 95% yield). $^1$H (500 MHz, CDCl$_3$) δ=11.72-11.62 (m, 1H), 8.34 (dt, J=8.32, 3.43 Hz, 1H), 7.44 (t, J=8.43 Hz, 1H), 6.96-6.88 (m, 1H), 5.42-5.28 (m, 1H), 5.13-4.85 (m, 2H), 3.94-3.80 (m, 1H), 3.74-3.60 (m, 1H), 3.22-3.18 (m, 2H), 2.05-1.62 (m, 6H), 1.31 (s, 9H), 1.24 (m, 9H). $^{13}$C NMR (125 MHz, CDCl$_3$) δ=177.86, 158.21, 158.19, 147.29, 135.03, 134.92, 115.90, 115.85, 115.80, 108.58, 108.53, 108.48, 108.43, 100.49, 99.18, 97.66, 64.70, 64.13, 64.10, 63.78, 63.57, 40.27, 38.25, 38.26, 36.51, 36.48, 35.93, 30.07, 27.64, 27.52, 24.71, 24.54, 24.47, 20.18, 19.92, 18.63. $^{31}$P (202 MHz, CDCl$_3$) δ=55.25

A solution of IIIa (61.5 g, 126 mmol) in THF (600 mL) was cooled to 0° C. Aqueous NaOH solution (132 mmol, 132 mL, 1M in water) was added slowly while keeping temperature below 5° C. After addition, the reaction mixture was stirred at room temperature for 17 h. The reaction mixture was diluted with water (300 mL). THF was removed under vacuum. The solid was collected to give 1-[3-tert-Butyl-3-oxo-4-(tetrahydro-pyran-2-yloxy)-2,3-dihydro-benzo[1,3]azaphosphol-1-yl]-2,2-dimethyl-propan-1-one (IIIb) the product (95% yield). $^1$H (400 MHz, CDCl$_3$) δ=7.91-7.82 (m, 1H), 7.42 (t, J=8.35 Hz, 1H), 6.98 (dd, J=8.22, 4.43 Hz, 0.3H, diasteriomer 1), 6.86 (dd, J=8.32, 4.40 Hz, 0.7H, diasteriomer 2), 5.73, (bs, 0.7H), 5.37 (bs, 0.3H), 4.35 (dd, J=13.72, 6.76 Hz, 1H), 4.03 (t, J=14.42 Hz, 1H), 3.95 (dq, J=10.33, 2.51 Hz, 1H), 3.70 (td, J=11.56, 3.36 Hz, 0.3H, diasteriomer 1), 3.55 (m, 0.7H, diasteriomer 2), 2.27-1.83 (m, 3H), 1.74-1.55 (m, 3H), 1.42 (s, 9H), 1.31-1.21 (m, 9h). $^{13}$C NMR (125 MHz, CDCl$_3$) δ=177.85, 135.03, 134.91, 115.84, 115.77, 108.57, 108.51, 99.16, 97.64, 64.77, 64.06, 63.77, 63.55, 40.27, 38.35, 38.26, 36.54, 30.06, 27.63, 27.51, 24.71, 24.54, 24.46, 20.18, 19.91. $^{31}$P (162 MHz, CDCl$_3$) δ=58.70

To a solution of IIIb (33.00 g; 83.87 mmol; 1.00 eq.) in methanol (165.00 ml) was charged PPTS (4.22 g; 16.77 mmol; 0.20 eq.). The mixture was heated at 50° C. for 2 h. After most of MeOH was removed by distillation, water was added. The product III was isolated as a white solid with 89% yield. $^1$H (400 MHz, CDCl$_3$) δ=9.98 (bs, 1H), 7.73 (dd, J=8.53, 3.14 Hz, 1H), 7.29 (t, J=8.26 Hz, 1H), 6.68 (dd, J=8.07, 4.46 Hz, 1H), 4.29 (dd, J=13.86, 5.72 Hz, 1H), 4.06 (t, J=14.06 Hz, 1H), 1.14 (s, 9H), 1.24 (d, J=16.48 Hz, 9H). $^{13}$C NMR (100 MHz, CDCl$_3$) δ=177.09, 177.05, 159.78, 150.49, 150.37, 135.92, 112.52, 112.46, 111.93, 111.84, 46.62, 45.99, 41.03, 34.23, 33.50, 28.25, 24.42. $^{31}$P (162 MHz, CDCl$_3$) δ=62.74

Example 2: Synthesis of (4s)-3-(tert-butyl)-4-(2,6-dimethoxyphenyl)-1,2-dihydrobenzo[d][1,3]azaphosphole 3-oxide (2c)

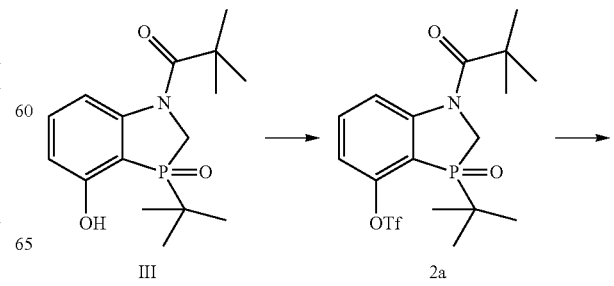

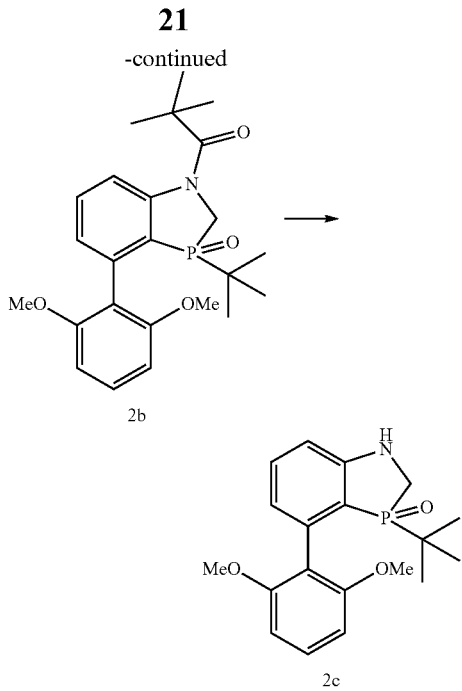

To a solution of 1-(3-(tert-butyl)-4-hydroxy-3-oxo-2-hydrobenzo[d][1,3]azaphosphol-1-yl)-2,2-dimethylpropan-1-one (III) (20.3 g, 65.5 mmol) and $CH_2Cl_2$ (30 mL) were charged TEA (18 mL, 131 mmol) and N-phenyl-bis(trifluoromethanesulfonimide) ($PhNTf_2$) (25.8 g, 72.1 mmol). The solution was stirred at room temperature for 1 h. Upon completion, the reaction mixture was cooled to 0° C., and washed with cold 5% NaOH aqueous solution (100 mL×2), cold 1M HCl (100 mL), and cold water (100 mL). The organic layer was dried with anhydrous $MgSO_4$ and concentrated. The residue was chased with hexanes. The solid was collected by filtration and washed with hexanes to give the product (2a) as a white solid (23.3 g, 81%). $^1$H (400 MHz, $CDCl_3$) δ=8.27 (dd, J=8.56, 2.19 Hz, 1H), 7.58 (t, J=8.42 Hz, 1H), 7.17 (dd, J=8.22, 3.73 Hz, 1H), 4.40 (dd, J=13.86, 6.97 Hz, 1H), 4.17 (dd, J=15.32, 14.05 Hz, 1H), 1.43 (s, 9H), 1.24 (d, J=16.53 Hz, 9H). $^{31}$P (162 MHz, $CDCl_3$) δ=57.91

To a solution of 3,5-dimethoxybenzene (3.09 g, 22.4 mmol) in THF (12 mL) at −5° C. was added n-BuLi while maintaining internal temperature below 1° C. After addition, the reaction mixture was warmed to room temperature and stirred for 2 h. the resulting solution was transferred to a stirred slurry of $ZnBr_2$ in THF at 0° C. The reaction mixture was then warmed to room temperature. After 30 minutes, it is ready for use.

After a solution of $Pd_2(dba)_3$ (0.01 mol %), ligand Ic (0.04 mol %) and triflate 2a (6.2 g) in THF was stirred for 15 minutes, the organozinc reagent from above was charged by cannula. After complete charge, the reaction mixture was heated at 70° C. for 30 minutes. Upon complete conversion, the reaction mixture was cooled to room temperature and filtered through a short pad of diatomaceous earth. The filtrate was concentrated and purified by column chromatography on silica gel using 0 to 20% EtOAc/Hexanes as eluent to afford 1-((4s)-3-(tert-butyl)-4-(2,6-dimethoxyphenyl)-3-oxido-2-hydrobenzo[d][1,3]azaphosphol-1-yl)-2,2-dimethylpropan-1-one (2b) as a gray solid (5.26 g, 87% yield). $^1$H (500 MHz, $CDCl_3$) δ=8.21 (dd, J=8.53, 3.13 Hz, 1H), 7.53 (t, J=7.93 Hz, 1H), 7.30 (t, J=8.40 Hz, 1H), 7.02 (dd, J=7.20, 3.30 Hz, 1H), 6.65 (d, J=8.40 Hz, 1H), 6.55 (d, J=8.35 Hz, 1H), 4.31 (dd, J=13.58, 7.28 Hz, 1H), 4.02 (t, J=14.03 Hz, 1H), 3.77 (s, 3H), 3.70 (s, 3H), 1.43 (s, 9H), 0.90 (d, J=15.55 Hz, 9H). $^{13}$C NMR (125 MHz, $CDCl_3$) δ=177.10, 177.07, 158.81, 157.43, 149.41, 149.29, 138.16, 138.12, 133.01, 132.99, 130.04, 127.97, 127.90, 119.65, 119.58, 118.92, 118.22, 116.89, 116.87, 104.24, 102.91, 55.83, 55.27, 46.33, 45.83, 41.00, 34.22, 33.66, 28.43, 28.30, 28.15, 23.60, 23.59. $^{31}$P (202 MHz, $CDCl_3$) δ=57.53

To a stirring solution of 2b (12.73 g, 29.64 mmol) in methanol (120 mL) at room temperature, sodium hydroxide (1M in water, 48 mmol) was charged. Then, the solution was heated to 50° C. for 1.5 h. The reaction was quenched with 2M HCl, adjusting pH to 7. After quenching, the solution was concentrated to form a slurry. The slurry was filtered and washed with water and recrystallized with cold DCM to give the product 2c as white solids (7.81 g, 77%). $^1$H (500 MHz, $CDCl_3$) δ=7.35 (dt, J=7.70, 0.85 Hz, 1H), 7.28 (t, J=8.25 Hz, 1H), 6.68-6.64 (m, 3H), 6.55 (d, J=8.35 Hz, 1H), 3.79 (s, 3H), 3.72 (s, 3H), 3.62-3.51 (m, 2H), 0.89 (d, J=15.60 Hz, 9H). $^{13}$C NMR (125 MHz, $CDCl_3$) δ=158.75, 157.45, 156.09, 155.94, 138.65, 138.60, 133.36, 133.35, 129.59, 122.38, 122.31, 118.09, 111.45, 111.39, 104.44, 102.98, 77.22, 56.01, 55.36, 53.42, 43.43, 42.91, 34.14, 33.57, 23.59, 23.58. $^{31}$P (202 MHz, $CDCl_3$) δ=64.68.

Example 3: Synthesis of (4s)-3-(tert-butyl)-4-(2,6-dimethoxyphenyl)-1,2-dihydrobenzo[d][1,3]azaphosphole (Id)

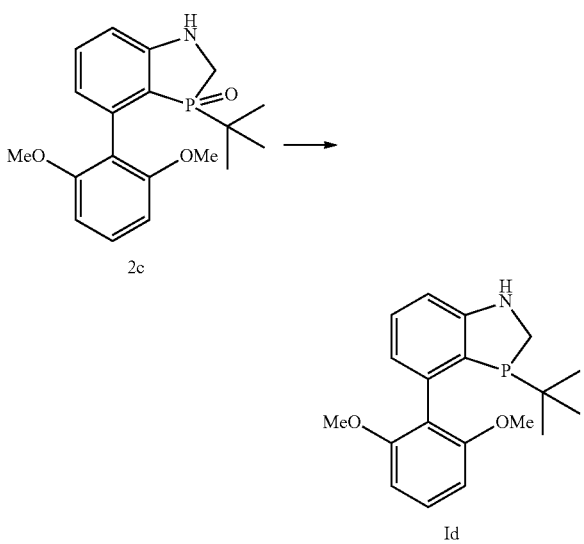

(4s)-3-(Tert-butyl)-4-(2,6-dimethoxyphenyl)-1,2-dihydrobenzo[d][1,3]azaphosphole 3-oxide (2c) (1.20 g, 3.47 mmol) was charged in an oven-dried flask, followed by vacuum-argon purging cycles three times. Toluene (24 mL), triethylamine (5.67 mL, 41.6 mmol) and trichlorosilane (2.8 mL, 28 mmol) were added sequentially. The reaction mixture was heated at 110° C. for 3 h. The reaction was quenched with 30% aqueous NaOH solution (20V) and stirred for 30 minutes. The solution was extracted with degassed MTBE or 1:1 EtOAc/$CH_2Cl_2$ (3×10 mL). Each extraction aliquot was passed through a column of aluminum oxide in vacuo. The filtrate was concentrated and dried completely under vacuum overnight to give the product Id as a white solid (0.92 g, 80% yield). $^1$H (400 MHz, $CDCl_3$)

δ=7.27 (t, J=8.34 Hz, 1H), 7.20 (t, J=7.68 Hz, 1H), 6.68 (d, J=7.92 Hz, 1H), 6.66-6.61 (m, 2H), 6.58 (d, J=8.24 Hz, 1H), 3.77 (s, 3H), 3.72 (s, 3H), 3.65-3.52 (m, 2H), 0.76 (d, J=11.92 Hz, 9H). $^{13}$C NMR (100 MHz, CDCl$_3$) δ=157.96, 157.20, 155.42, 138.75, 138.57, 129.80, 128.72, 121.41, 120.24, 108.70, 104.45, 103.61, 55.98, 55.96, 55.40, 43.58, 43.39, 31.53, 31.34, 29.71, 26.95, 26.80, 23.60. $^{31}$P (162 MHz, CDCl$_3$) δ=−0.17.

Example 4: Synthesis of 3-tert-Butyl-4-(2,6-dimethoxy-phenyl)-1-phenyl-2,3-dihydro-1H-benzo[1,3]azaphosphole (Ig)

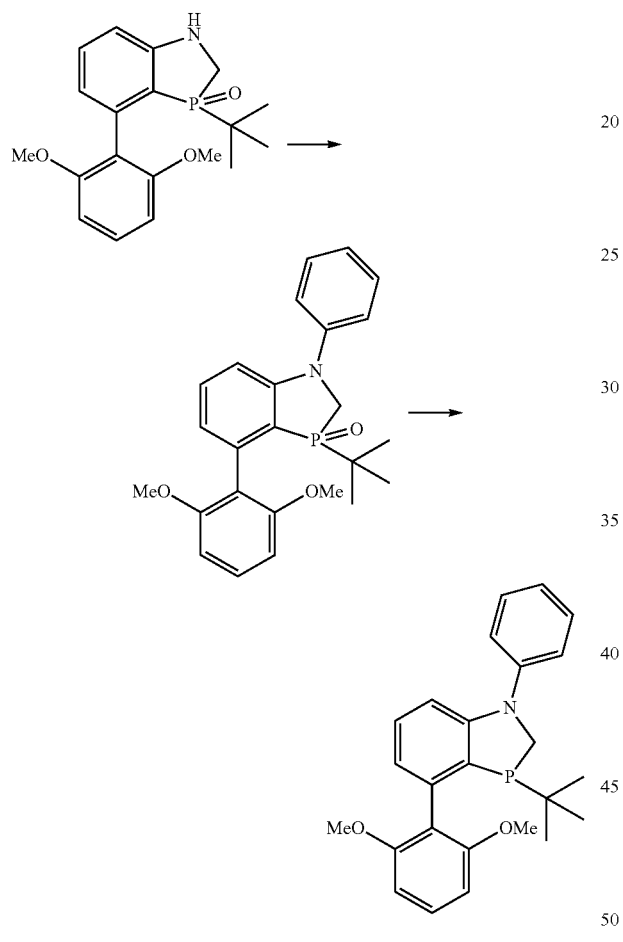

An inerted flask was charged with (4s)-3-(tert-butyl)-4-(2,6-dimethoxyphenyl)-1,2-dihydrobenzo[d][1,3]azaphosphole 3-oxide (1.00 g, 2.89 mmol), Pd$_2$dba$_3$ (0.066 g, 0.072 mmol), RuPHOS (0.135 g, 0.289 mmol), and sodium t-butoxide (0.33 g, 3.5 mmol). The flask was backfilled with nitrogen thrice. Phenyl bromide (0.35 mL, 3.5 mmol), and THF (10 mL) were added, followed by backfilling with nitrogen thrice. The reaction mixture was stirred at rt for 5 minutes and heated at 67° C. for 1 h. The reaction mixture was passed through a pad of diatomaceous earth and washed with THF (3×10 mL). The crude was concentrated and purified by column chromatography by silica gel using 0 to 8% methanol in dichloromethane to obtain (4s)-3-(tert-butyl)-4-(2,6-dimethoxyphenyl)-1-phenyl-1,2-dihydrobenzo[d][1,3]azaphosphole 3-oxide as a brown solid (0.92 g, 75% yield). $^1$H (500 MHz, CDCl$_3$) δ=7.39 (t, J=7.83 Hz, 2H), 7.33-7.27 (m, 4H), 7.14 (t, J=7.15 Hz, 1H), 6.94 (dd, J=8.25, 3.30 Hz, 1H), 6.70-6.66 (m, 2H), 6.56 (d, J=8.35 Hz, 1H), 4.07 (t, J=14.10 Hz, 1H), 3.82 (s, 3H), 3.78 (dd, J=13.60, 5.50 Hz, 1H), 3.75 (s, 3H), 0.93 (d, J=15.50 Hz, 9H). $^{13}$C NMR (125 MHz, CDCl$_3$) δ=158.83, 157.49, 153.56, 153.44, 143.81, 143.76, 139.16, 139.12, 133.09, 133.07, 129.72, 129.53, 124.29, 122.72, 122.61, 122.54, 117.75, 117.72, 115.91, 115.21, 109.88, 109.81, 104.43, 102.98, 56.00, 55.36, 50.21, 49.69, 34.11, 33.54, 23.62, 23.61. $^{31}$P (202 MHz, CDCl$_3$) δ=58.45.

The above intermediate (0.40 g, 0.95 mmol) was charged in an oven-dried flask, followed by vacuum-argon purging cycles three times. Toluene (8 mL), triethylamine (1.6 mL, 11 mmol) and trichlorosilane (0.77 mL, 7.6 mmol) were added sequentially. The reaction mixture was heated at 110° C. for 2 h. The reaction was quenched with 30% aqueous NaOH solution (10 mL) and stirred for 30 minutes. The solution was extracted with degassed 1:1 EtOAc/CH$_2$Cl$_2$ (3×5 mL). Each extraction aliquot was passed through a column of aluminum oxide in vacuo. The filtrate was concentrated and dried completely under vacuum overnight to give the product Ig as a yellow solid (0.274 g, 72% yield). $^1$H (500 MHz, CDCl$_3$) δ=7.38-7.27 (m, 5H), 7.21 (t, J=7.80 Hz, 1H), 7.06-6.98 (m, 2H), 6.72-6.64 (m, 2H), 6.60 (d, J=8.35 Hz, 1H), 4.21 (dd, J=23.03, 12.68 Hz, 1H), 3.81-3.70 (m, 7H), 0.76 (d, J=11.95 Hz, 9H). $^{13}$C NMR (125 MHz, CDCl$_3$) δ=158.82, 158.05, 157.49, 157.17, 153.47, 151.10, 151.08, 144.84, 144.82, 143.74, 139.47, 139.32, 139.16, 139.12, 133.11, 133.10, 129.72, 129.60, 129.59, 129.53, 129.14, 129.04, 128.85, 128.29, 127.25, 127.15, 125.30, 124.31, 122.73, 122.62, 122.54, 122.07, 121.84, 121.80, 120.31, 119.93, 119.91, 109.88, 109.82, 108.77, 104.52, 104.43, 103.62, 102.97, 77.22, 56.00, 55.97, 55.96, 55.40, 55.36, 50.40, 50.23, 50.17, 49.65, 34.10, 33.53, 31.24, 30.91, 30.75, 26.69, 26.57, 23.62, 23.61, 21.46. $^{31}$P (202 MHz, CDCl$_3$) δ=−16.81.

Example 5: Synthesis of 3-tert-Butyl-4-(2,6-dimethoxy-phenyl)-1-(4-methoxy-phenyl)-2,3-dihydro-1H-benzo[1,3]azaphosphole (Ie)

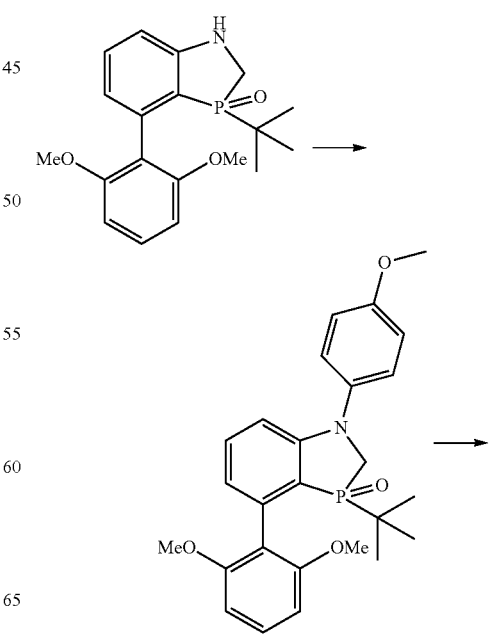

-continued

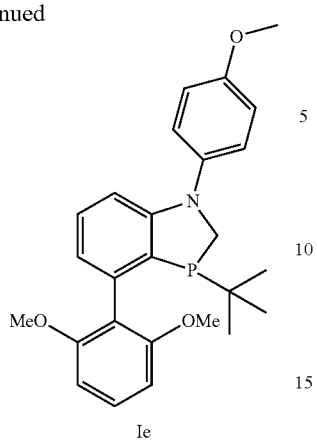

Ie

An inerted flask was charged with (4s)-3-(tert-butyl)-4-(2,6-dimethoxyphenyl)-1,2-dihydrobenzo[d][1,3]azaphosphole 3-oxide (0.100 g, 0.289 mmol), Pd$_2$dba$_3$ (0.0067 g, 0.0072 mmol), RuPHOS (0.0135 g, 0.0289 mmol), and sodium t-butoxide (0.033 g, 0.35 mmol). The flask was backfilled with nitrogen thrice. 4-bromoanisole (0.05 mL, 0.35 mmol), and THF (1 mL) were added, followed by backfilling with nitrogen thrice. The reaction mixture was stirred at rt for 5 minutes and heated at 67° C. for 6 h. The reaction mixture was passed through a pad of celite and washed with THF (3×1 mL). The crude was concentrated and purified by column chromatography by silica gel using 0 to 10% methanol in dichloromethane to obtain (4s)-3-(tert-butyl)-4-(2,6-dimethoxyphenyl)-1-(4-methoxyphenyl)-1,2-dihydrobenzo[d][1,3] azaphosphole 3-oxide as a yellow solid (85 mg, 65% yield). $^1$H (500 MHz, CDCl$_3$) δ=7.31-7.27 (m, 2H), 7.22 (d, J=8.80 Hz, 2H), 6.94 (d, J=8.80 Hz, 2H), 6.69-6.61 (m, 3H), 6.56 (d, J=8.85 Hz, 2H), 3.95 (t, J=14.28 Hz, 1H), 3.84 (s, 3H), 3.83 (s, 3H), 3.77-3.73 (m, 4H), 0.94 (d, J=15.41 Hz, 9H). $^{13}$C NMR (125 MHz, CDCl$_3$) δ=158.83, 157.52, 157.15, 155.03, 154.91, 138.88, 138.84, 136.91, 136.85, 133.17, 133.16, 129.65, 127.80, 125.82, 121.84, 121.76, 117.97, 117.95, 114.99, 114.94, 109.46, 109.39, 104.44, 104.19, 102.99, 56.01, 55.65, 55.55, 50.82, 50.31, 34.21, 33.64, 23.67, 23.66, 23.34. $^{31}$P (202 MHz, CDCl$_3$) δ=58.75.

The above intermediate (0.358 g, 0.792 mmol) was charged in an oven-dried flask, followed by vacuum-argon purging cycles three times. Toluene (7 mL), triethylamine (1.3 mL, 9.6 mmol) and trichlorosilane (0.65 mL, 6.4 mmol) were added sequentially. Then, the reaction mixture was heated at 110° C. for 2 h. The reaction was quenched with 30% aqueous NaOH solution (10 mL) and stirred for 30 minutes. The solution was extracted with degassed 1:1 EtOAc/CH$_2$Cl$_2$ (3×5 mL). Each extraction aliquot was passed through an inerted column of aluminum oxide in vacuo. The filtrate was concentrated and dried completely under vacuum overnight to give the product (Ie) as a yellow solid (0.234 g, 68% yield, contains 20% starting material, easily oxidized). HRMS (ESI+/TOF): m/z calcd for C$_{26}$H$_{31}$NO$_4$P$^+$ [M+O+H]$^+$ 452.1985, found 452.1969.

Example 6: Synthesis of 3-(tert-butyl)-4-(2,6-dimethoxyphenyl)-1-(4-(trifluoromethyl)phenyl)-1,2-dihydrobenzo[d][1,3]azaphosphole (If)

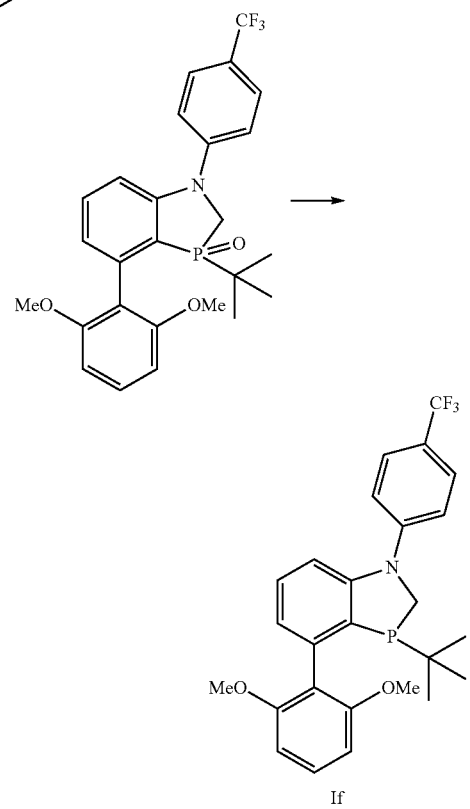

If

An inerted flask was charged with (4s)-3-(tert-butyl)-4-(2,6-dimethoxyphenyl)-1,2-dihydrobenzo[d][1,3]azaphosphole 3-oxide (5.00 g, 14.5 mmol), Pd$_2$dba$_3$ (0.199 g, 0.217 mmol), RuPHOS (0.405 g, 0.867 mmol), and sodium t-butoxide (1.67 g, 17.34 mmol). The flask was backfilled with nitrogen thrice. 4-Bromobenzotriflouride (2.43 mL, 17.34 mmol), and THF (50 mL) were added, followed by backfilling with nitrogen thrice. The reaction mixture was stirred at rt for 5 minutes and heated at 67° C. for 3 h. The reaction mixture was passed through a pad of celite and washed with THF (3×50 mL). The crude was concentrated and purified by column chromatography by silica gel using 0 to 4% methanol in dichloromethane to obtain 3-(tert-butyl)-4-(2,6-dimethoxyphenyl)-1-(4-(trifluoromethyl)phenyl)-1,2-dihydrobenzo[d][1,3]azaphosphole 3-oxide as yellow solid (4.53 mg, 64% yield). $^1$H (400 MHz, CDCl$_3$) δ=7.61 (d, J=8.52 Hz, 2H), 7.42-7.34 (m, 3H), 7.31 (t, J=8.38 Hz, 1H), 7.15 (dd, J=8.34, 3.50 Hz, 1H), 6.79 (dd, J=7.40, 3.48 Hz, 1H), 6.67 (d, J=8.32 Hz, 2H), 6.57 (d, J=8.32 Hz, 2H), 4.12 (t, J=13.76 Hz, 1H), 3.85-3.72 (m, 7H), 0.93 (t, J=15.65 Hz, 9H). $^{13}$C NMR (100 MHz, CDCl$_3$)=158.76, 157.44, 151.74, 151.59, 146.81, 146.75, 139.65, 139.60, 133.14, 133.12, 129.92, 126.75, 126.71, 126.67, 126.64, 125.52, 124.99, 124.66, 124.20, 124.10, 122.82, 120.56, 117.49, 117.32, 117.29, 116.60, 110.61, 110.53, 104.41, 102.99, 55.97, 55.36, 50.01, 49.37, 34.09, 33.38, 23.57. $^{31}$P (162 MHz, CDCl$_3$) δ=57.64

The above intermediate (0.88 g, 1.8 mmol) was charged in an oven-dried flask, followed by vacuum-argon purging cycles three times. Toluene (18 mL), triethylamine (3.0 mL, 22 mmol) and trichlorosilane (1.45 mL, 14.4 mmol) were added sequentially. The reaction mixture was heated at 110° C. for 2 h. The reaction was quenched with 30% aqueous NaOH solution (20 mL) and stirred for 30 minutes. The solution was extracted with degassed 1:1 EtOAc/CH$_2$Cl$_2$ (3×10 mL). Each extraction aliquot was passed through a column of aluminum oxide in vacuo. The filtrate was concentrated and dried completely under vacuum overnight to give the product (If) as a yellow solid (0.73 g, 86% yield). $^1$H (400 MHz, CDCl$_3$) δ=7.49 (d, J=Hz, 2H), 7.29 (d, J=Hz, 2H), 7.23 (t, J=Hz, 1H), 7.19-7.10 (m, 2H), 6.77 (ddd, J=Hz, 1H), 6.66 (d, J=8.28 Hz, 1H), 6.60 (d, J=8.40 Hz, 1H), 4.24 (dd, J=23.05, 12.72 Hz, 2H), 3.80-3.70 (m, 7H), 0.72 (d, J=12.04 Hz, 9H). $^{13}$C NMR (100 MHz, CDCl$_3$) δ=133.13, 129.92, 129.65, 129.06, 126.66, 126.45, 126.41, 123.41, 123.36, 120.57, 118.37, 110.60, 109.90, 104.51, 103.64, 102.98, 55.95, 55.40, 50.37, 50.15, 30.69, 23.57. $^{31}$P (162 MHz, CDCl$_3$) δ=−17.20.

Example 7: Synthesis of 3-(tert-butyl)-4-(2,6-dimethoxyphenyl)-N-phenyl-2-hydrobenzo[d][1,3]azaphosphole-1-carboxamide (Ih)

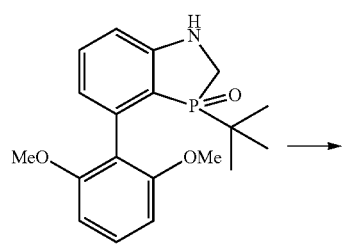

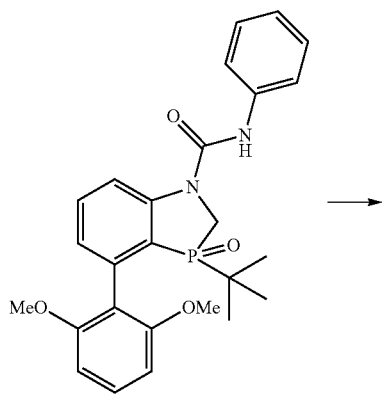

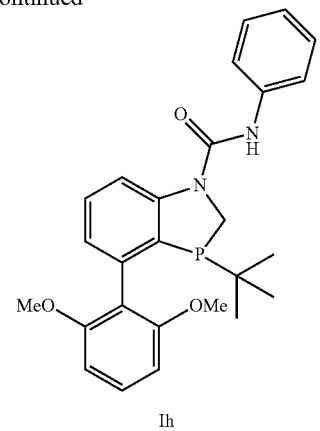

Ih

An inerted flask was charged with 3-(tert-butyl)-4-(2,6-dimethoxyphenyl)-1,2-dihydrobenzo[d][1,3]azaphosphole 3-oxide (1.00 g, 2.89 mmol) and backfilled with nitrogen thrice. Phenyl isocyanate (0.94 mL, 8.7 mmol), Hünig's base (0.60 mL, 3.5 mmol), and THF (10 mL) were charged into the flask and the flask backfilled again with nitrogen thrice. The reaction mixture was kept stirring at 77° C. overnight. THF was removed in vacuo followed by the addition of dichloromethane (20 mL) to crash out excess phenyl isocyanate. The solids were filtered and washed with dichloromethane (2×20 mL). The filtrate was concentrated and purified by column chromatography on silica gel using 0 to 8% methanol in dichloromethane to obtain 3-(tert-butyl)-4-(2,6-dimethoxyphenyl)-N-phenyl-2-hydrobenzo[d][1,3]azaphosphole-1-carboxamide 3-oxide as white solid (1.13 g, 84% yield).

To an oven-dried flask, the above intermediate (0.500 g, 1.08 mmol) was charged, followed by vacuum-argon purging cycles three times. Toluene (10 mL), triethylamine (1.8 mL, 13 mmol) and trichlorosilane (0.87 mL, 1.2 mmol) were added sequentially. The reaction mixture was heated at 110° C. for 2 h. The reaction was quenched with 30% aqueous NaOH solution (10 mL) and stirred for 30 minutes. The solution was extracted with degas sed 1:1 EtOAc/CH$_2$Cl$_2$ (3×5 mL). Each extraction aliquot was passed through a column of aluminum oxide in vacuo. The filtrate was concentrated and dried completely under vacuum overnight to give the product (Ih) as a white solid (0.38 g, 79% yield). $^1$H (400 MHz, CDCl$_3$) δ=7.78 (d, J=8.20 Hz, 1H), 7.47 (d, J=7.72 Hz, 2H), 7.41 (t, J=7.88 Hz, 1H), 7.36-7.28 (m, 3H), 7.09 (t, J=7.38 Hz, 1H), 6.97 (dd, J=7.56, 3.32 Hz, 1H), 6.94 (s, 1H), 6.66 (d, J=8.36 Hz, 1H), 6.60 (d, J=8.36 Hz, 1H), 4.20 (dd, J=12.84, 2.32 Hz, 1H), 3.98 (dd, J=12.86, 22.51 Hz, 1H), 3.76 (s, 3H), 3.73 (s, 3H), 0.75 (d, J=12.08 Hz, 9H). $^{31}$P (162 MHz, CDCl$_3$) δ=−15.85.

Example 8: Synthesis of 1-(3-(tert-butyl)-4-(2,6-dimethoxyphenyl)-2-hydrobenzo[d][1,3]azaphosphol-1-yl)-2,2-dimethylpropan-1-one (Ic)

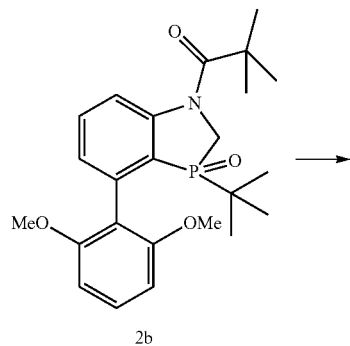

2b

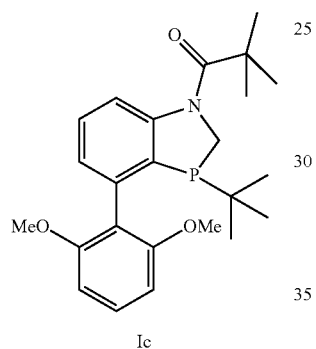

Ic 1-(3-(tert-Butyl)-4-(2,6-dimethoxyphenyl)-3-oxido-2-hydrobenzo[d][1,3]azaphosphol-1-yl)-2,2-dimethylpropan-1-one (2b, Example 2) (1.00 g, 2.32 mmol) was charged in an oven-dried flask, followed by vacuum-argon purging cycles three times. Toluene (20 mL), triethylamine (3.8 mL, 29 mmol) and trichlorosilane (1.88 mL, 18.6 mmol) were added sequentially. Then, the reaction mixture was heated at 110° C. and stirred at this temperature for 3 h. The reaction was quenched with 30% aqueous NaOH solution (20V) and stirred for 30 minutes. The solution was extracted with degassed MTBE or 1:1 EtOAc/CH$_2$Cl$_2$ (3×10 mL). Each extraction aliquot was passed through a column of aluminum oxide in vacuo. The filtrate was concentrated and dried completely under vacuum overnight to give the product (Ic) as a white solid (0.89 g, 92% yield). $^1$H (500 MHz, CDCl$_3$) δ=8.05 (d, J=8.40 Hz, 1H), 7.30 (t, J=7.93 Hz, 1H), 7.22 (t, J=8.35 Hz, 1H), 6.90 (dd, J=7.28, 3.23 Hz, 1H), 6.54 (dd, J=28.78, 8.33 Hz, 1H), 4.30 (dd, J=13.03, 2.03 Hz, 1H), 3.91 (dd, J=20.88, 13.02 Hz, 1H), 3.66 (s, 3H), 3.62 (s, 3H), 1.37 (s, 9H), 0.65 (d, J=12.00 Hz, 9H). $^{13}$C NMR (125 MHz, CDCl$_3$) δ=176.67, 176.65, 158.05, 148.99, 148.97, 138.22, 138.06, 130.05, 129.66, 129.65, 129.11, 129.04, 128.99, 126.73, 126.69, 119.54, 119.52, 118.98, 104.41, 104.24, 103.64, 102.91, 55.85, 55.84, 55.33, 55.27, 46.87, 46.69, 41.00, 40.80, 31.93, 31.46, 31.30, 31.25, 29.70, 29.66, 29.37, 28.34, 26.82, 26.70, 23.60, 22.70, 14.12. $^{31}$P (202 MHz, CDCl$_3$) δ=−11.51.+

Example 9: Synthesis of 1-[3,3'-Di-tert-butyl-1'-(2,2-dimethyl-propionyl)-3'-oxo-2,3,2',3'-tetrahydro-1'H-3'lambda*5*-[4,4']bi[benzo[1,3]azaphospholyl]-1-yl]-2,2-dimethyl-propan-1-one (Ii)

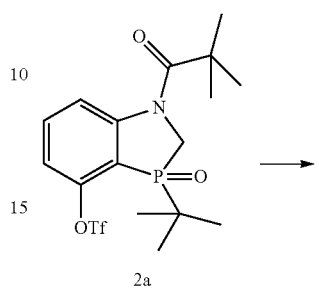

2a

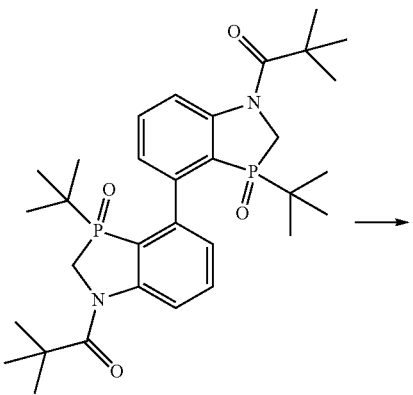

9a

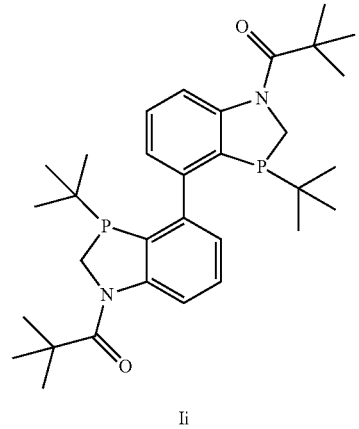

Ii

A flask was charged with 3-(tert-butyl)-3-oxido-1-pivaloyl-1,2-dihydrobenzo[d][1,3] azaphosphol-4-yl trifluoromethanesulfonate (2a) (1.33 g, 3.01 mmol), potassium bromide (0.714 g, 6.03 mmol), zinc powder (0.59 g, 9.04 mmol), Pd$_2$dba$_3$ (0.083 g, 0.09 mmol), and XPhos (0.115 g, 0.24 mmol). The flask was backfilled with nitrogen thrice after the addition of solids. DMAC (4.5 mL) was charged and the flask backfilled thrice again with nitrogen. The solution was stirred at 140° C. for 1 h. The solution was cooled to room temperature and passed through a pad of diatomaceous earth. The filtrate was diluted with dichloromethane (50 mL) washed with 1M NaOH (2×20 mL) and water (20 mL). The combined organic layers were dried (MgSO$_4$), filtered and concentrated and purified by column chromatography on silica gel using 0 to 5% methanol in dichloromethane as eluent to obtain 1,1'-(3,3'-di-tert-butyl-3,3'-dioxido-2,2'-dihydro-[4,4'-bibenzo[d][1,3]azaphosphole]-1,1'-diyl)bis(2,2-dimethylpropan-1-one) (9a) as a yellow solid (0.378 g, 43%). $^1$H (400 MHz, CDCl$_3$) δ=8.33 (dd, J=8.08, 2.88 Hz, 1H), 8.23 (dd, J=7.44, 3.96 Hz, 1H), 8.12 (dd, J=8.86, 2.60 Hz, 1H), 7.26 (t, J=7.88 Hz, 1H), 7.50 (t, J=8.06 Hz, 1H), 7.17, (dd, J=7.26, 2.98 Hz, 1H), 4.43 (dd, J=13.54, 6.46 Hz, 1H), 4.37-4.20 (m, 2H), 4.08 (t, J=14.28 Hz, 1H), 1.44 (s, 9H), 1.42 (s, 9H), 0.92 (d, J=15.92 Hz, 9H), 0.83 (d, J=14.96 Hz, 9H). $^{13}$C NMR (100 MHz, CDCl$_3$)=133.42, 132.20, 130.00, 129.93, 125.61, 125.52, 121.74, 120.45, 46.72, 46.06, 45.17, 41.06, 28.30, 24.15, 24.07. $^{31}$P (162 MHz, CDCl$_3$) δ=61.82. 9a (0.100 g, 0.171 mmol) was charged into an oven-dried flask, followed by vacuum-argon purging cycles three times. Toluene (2 mL), triethylamine (0.29 mL, 2.05 mmol) and trichlorosilane (0.14 mL, 1.37 mmol) were added sequentially. The reaction mixture was heated at 110° C. for 2 h. The reaction was quenched with 30% aqueous NaOH solution (10 mL) and stirred for 30 minutes. The product was extracted with degassed 1:1 EtOAc/CH$_2$Cl$_2$ (3×5 mL). The extraction solution was passed through a column of aluminum oxide in vacuo. The elute was concentrated and dried completely under vacuum overnight to give the product (Ii) as a white solid (0.070 g, 72% yield). $^1$H (400 MHz, CD$_2$Cl$_2$) δ=8.07 (d, J=Hz, 2H), 7.30 (t, J=Hz, 2H), 7.01 (d, J=Hz, 2H), 4.29 (d, J=Hz, 2H), 4.03-3.90 (m, 2H), 1.35 (s, 18H), 0.58-0.51 (m, 18H). $^{13}$C NMR (100 MHz, CD$_2$Cl$_2$) δ=176.87, 149.54, 145.38, 130.01, 125.60, 118.94, 46.43, 46.30, 46.18, 40.79, 31.58, 28.08, 28.03, 26.96, 26.88. $^{31}$P (162 MHz, CD$_2$Cl$_2$) δ=−10.83.

Example 10: Synthesis of 3-tert-Butyl-4-methoxy-1-phenyl-2,3-dihydro-1H-benzo[1,3]azaphosphole (Ip)

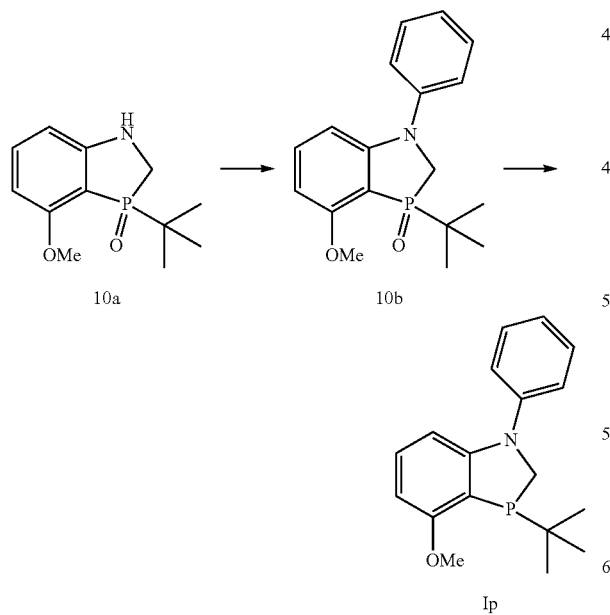

An inerted flask was charged with 3-(tert-butyl)-4-methoxy-1,2-dihydrobenzo[d][1,3]azaphosphole 3-oxide (10a) (1.00 g, 4.18 mmol), Pd$_2$dba$_3$ (0.0962 g, 0.105 mmol), RuPHOS (0.1951 g, 0.418 mmol), and sodium t-butoxide (0.482 g, 5.01 mmol). The flask was backfilled with nitrogen thrice. Phenyl bromide (0.51 mL, 5.01 mmol), and THF (10 mL) were added, followed by backfilling with nitrogen thrice. The reaction mixture was stirred at rt for 5 minutes and heated at 67° C. overnight. The reaction mixture was passed through a pad of celite and washed with THF (3×50 mL). The crude was concentrated and purified by column chromatography by silica gel using 0 to 6% methanol in dichloromethane to obtain 10b as yellow solid (1.29 mg, 98% yield). $^1$H (400 MHz, CDCl$_3$) δ=7.41-7.35 (m, 2H), 7.27-7.14 (m, 4H), 6.48 (dd, J=8.32, 3.01 Hz, 1H), 6.29 (dd, J=8.12, 4.52 Hz, 1H), 4.03 (t, J=14.52 Hz, 1H), 3.88 (s, 3H), 3.85 (dd, J=13.99, 4.27 Hz, 1H), 1.29 (d, J=16.05 Hz, 9H). $^{13}$C NMR (100 MHz, CDCl$_3$)=143.56, 135.72, 129.59, 124.95, 123.42, 104.31, 104.22, 100.71, 100.64, 55.37, 50.77, 50.14, 34.36, 33.62, 24.46. $^{31}$P (162 MHz, CDCl$_3$) δ=60.37

Intermediate 10b was reduced by the procedure described in Example 9 to produce Ip. $^1$H (500 MHz, CDCl$_3$) δ=7.27-7.18 (m, 4H), 7.05 (m, 1H), 6.96 (m, 1H), 6.57 (m, 1H), 6.26 (m, 1H), 3.88 (s, 3H), 4.11-4.04 (m, 1H), 3.77-3.74 (m, 4H), 0.92 (d, J=11.85 Hz, 9H). $^{31}$P (202 MHz, CDCl$_3$) δ=−23.65. MS (M+H)+: 300.3.

Example 11: Synthesis of 3-tert-Butyl-4-methoxy-2,3-dihydro-benzo[1,3]azaphosphole-1-carboxylic acid phenylamide (Io)

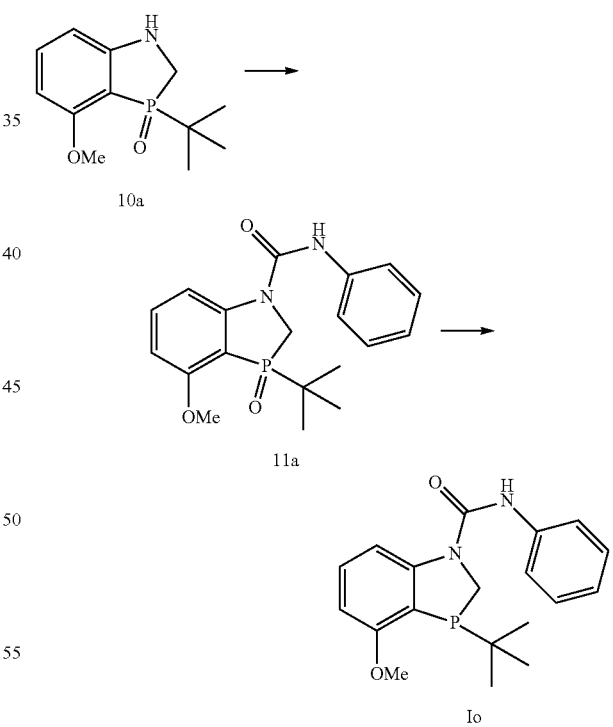

An inerted flask was charged with 3-(tert-butyl)-4-methoxy-1,2-dihydrobenzo[d][1,3]azaphosphole 3-oxide (10a) (0.500 g, 2.09 mmol) and backfilled with nitrogen thrice. Phenyl isocyanate (0.68 mL, 6.3 mmol), Hünig's base (0.44 mL, 2.5 mmol), and THF (5 mL) were charged into the flask and the flask was vacuumed and backfilled again with nitrogen three times. The reaction mixture was stirred at 77° C. overnight. THF was removed in vacuo followed by the addition of dichloromethane (20 mL) to crash out excess phenyl isocyanate. The solid was filtered and washed with dichloromethane (2×20 mL). The filtrate was concentrated and purified by column chromatography on silica gel using 0 to 8% methanol in dichloromethane to give (11a) as a white solid (0.77 g, 100% yield). $^1$H (400 MHz, CDCl$_3$) δ=8.85 (s, 1H), 7.58 (dd, J=8.60, 1.04 Hz, 2H), 7.41-7.27 (m, 4H), 7.04 (tt, J=7.36, 1.09 Hz, 1H), 3.78 (dd, J=7.98, 4.58 Hz, 1H), 4.57 (t, J=15.04 Hz, 1H), 3.91 (dd, J=14.36, 3.56 Hz, 1H), 3.44 (s, 3H), 1.26 (d, J=16.61 Hz, 9H). $^{13}$C NMR (100 MHz, CDCl$_3$)=160.57, 153.51, 153.44, 150.34, 139.15, 136.47, 128.60, 122.96, 119.73, 110.37, 110.28, 104.72, 103.85, 103.65, 103.59, 54.93, 45.30, 44.67, 34.07, 33.31, 24.70. $^{31}$P (162 MHz, CDCl$_3$) δ=59.74

Intermediate 111a was reduced by the procedure described in Example 9 to produce Io. $^1$H (500 MHz, CDCl$_3$) δ=7.52 (d, J=8.15 Hz, 1H), 7.45 (d, J=7.95 Hz, 2H), 7.34-7.32 (m, 2H), 7.26 (bs, 1H), 7.11-7.08 (m, 1H), 6.87 (bs, 1H), 6.61-6.58 (m, 1H), 4.18 (dd, J=2.6, 12.6 Hz, 1H), 3.98-3.91 (m, 1H), 3.86 (s, 3H), 1.00 (d, J=12.3 Hz, 9H). $^{31}$P (202 MHz, CDCl$_3$) δ=−22.04. MS (M+H)+: 343.3.

Applications of the Ligands

The following examples illustrate the utility of the ligands in various organic reactions.

Example 12: Negishi Coupling. Synthesis of 2,2'-Dimethyl-1,1'-binaphthalene using Ligand Idd

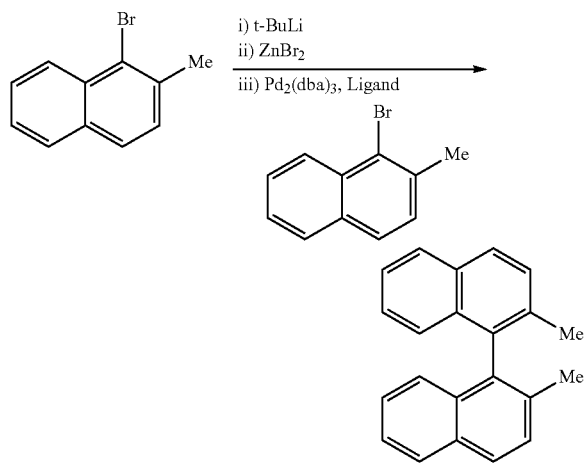

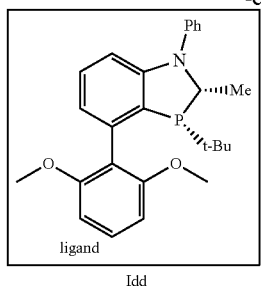

A crimp-cap vial with a magnetic stir-bar was charged with 1-bromo-2-methylnaphthalene (106 mg, 0.43 mmol) and sealed. THF (1 mL) was added and the vial was immersed in a dry ice/acetone bath (−78° C.). A 1.55 M solution of t-BuLi (0.57 mL, 0.88 mmol) was charged dropwise over 2 min. The reaction mixture becomes thick and chalky and is allowed to stir for 1 h. In a second crimp-cap vial was prepared a solution of ZnBr$_2$ (136 mg, 0.6 mmol) in THF (1 mL). The ZnBr$_2$ solution was added to the reaction mixture at −78° C. and then warmed to rt and allowed to stir for 15 min before use. In a third crimp-cap vial with stir-bar were charged the arylbromide (70 mg, 0.289 mmol, 1 eq), Pd$_2$(dba)$_3$ (6.6 mg, 0.0072 mmol, 2.5 mol %), and ligand Idd (12.2 mg, 0.029 mmol, 10 mol %). The mixture was inerted with Ar using vacuum-purge cycles. THF (1 mL) was then added, and the mixture was allowed to stir for 10 min. The zincate solution was then transferred to the catalyst/bromide solution by syringe. The final mixture was then immersed in an oil bath at 60° C. After 12 hours, the reaction was cooled to rt and quenched with 2M HCl (5 mL). DCM (10 mL) was then added. The layers were separated, and the aqueous phase was extracted with DCM (1×50 mL). The combined organics were washed with 20% citric acid solution, rinsed with brine, dried with MgSO$_4$, and concentrated in vacuo. Purification of the crude mixture by flash chromatography (gradient, 0-50% DCM in hexanes) afforded 78.6 mg (96%) of a colorless oil. $^1$H NMR (500 Hz, CDCl$_3$) 7.85 (m, 4H), 7.47 (d, J=8.5 Hz, 2H), 7.35 (t, J=7.0 Hz, 2H), 7.16 (t, J=7.0 Hz, 2H), 7.04 (d, J=8.6 Hz, 2H), 2.02 (s, 6H).

Example 13: Synthesis of Ligands Iu, Iv and Ix

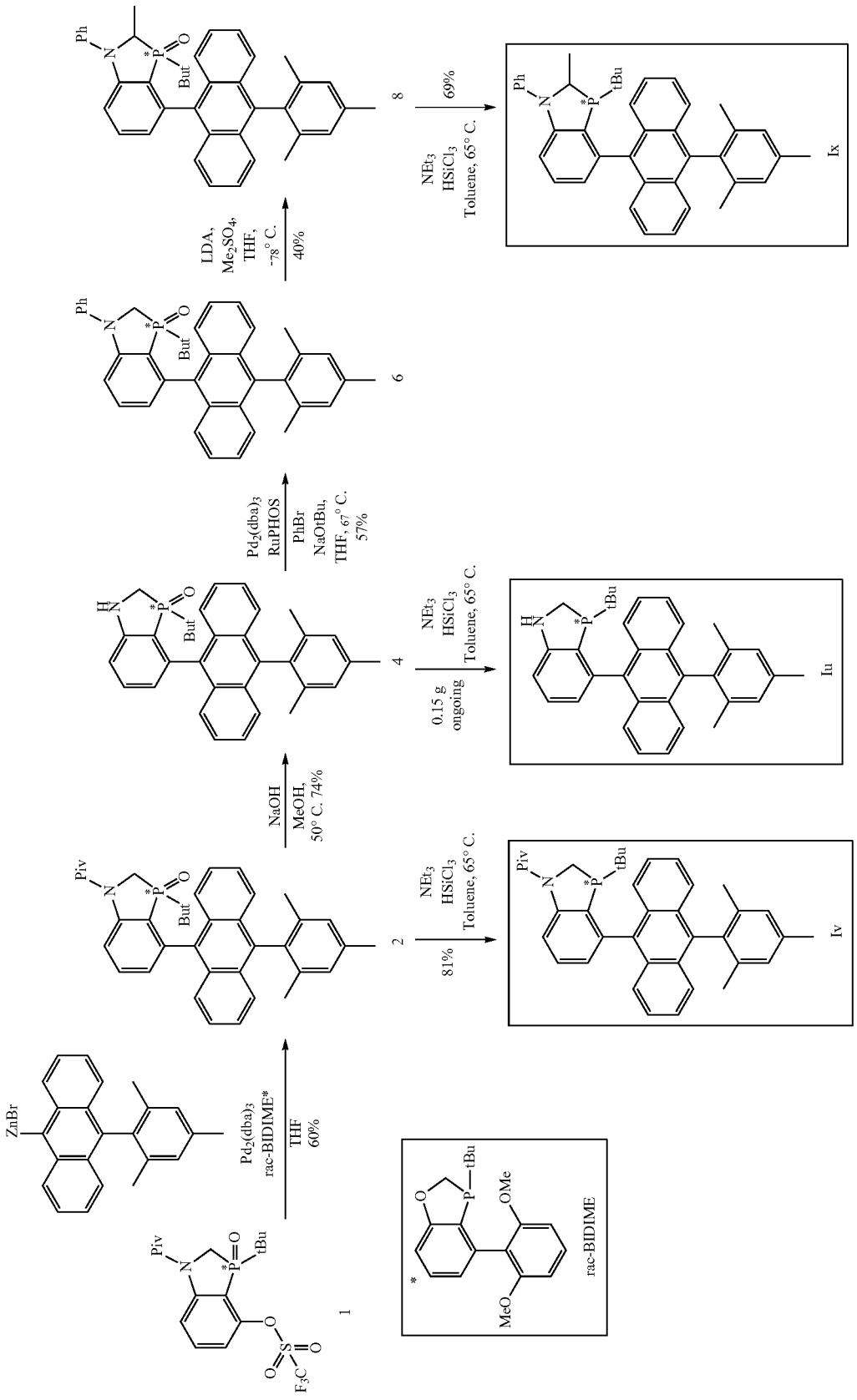

A 100 mL 2-neck round-bottom flask with magnetic stir-bar and fitted with a reflux condenser with a short-path distillation head was purged with $N_2$. Then 9-bromo-10-mesitylanthraene (7.00 g, 18.66 mmol) and THF (24 mL) were charged to the flask. The solution was cooled to −78° C. in a dry ice acetone bath. t-BuLi (1.58 M in pentane, 38.24 mmol) was then added dropwise over 20 min. The resulting yellow slurry was stirred at −78° C. for 10 min and then allowed to warm to rt and stirred for an additional 15 min before use. $ZnBr_2$ (5.17 g, 22.94 mmol) in THF (17 mL) was then transferred by cannula to the aryllithium reagent at rt, and the mixture was allowed to stir for an additional 20 min. A solution of triflate 1 (4.0, 9.10 mmol), $Pd_2(dba)_3$ (0.167 g, 0.182 mmol), and rac-BIDIME (0.181 g, 0.546 mmol) in THF (2 mL) was prepared in the glove box. The vial was sealed with a septum. The catalyst/triflate solution was then transferred to the ArZnBr solution using cannula transfer. The final mixture was then immersed in an oil bath at 65° C. heated for 2.5 h before analyzing it by UPLC/MS. The solvent was removed under reduced pressure. 100 mL of DCM was added. Then 30 mL of 20% citric acid solution was added. Organic layer was separated. The aqueous layer was washed with DCM (3×30 mL). The organic layers were collected together, dried with $Na_2SO_4$ and purified flash chromatography (5% MeOH in DCM). 60% isolated yield of 2 was achieved.

$^1$H NMR (500 MHz, $CDCl_3$) δ 8.67 (d, J=8.67, 1H), 7.81-7.86 (m, 2H), 7.53 (d, J=7.53, 1H), 7.27-7.48 (m, 6H), 7.16 (m, 1H), 7.10 (d, J=15.45, 2H), 4.42-4.46 (m, 1H), 4.24-4.30 (m, 1H), 2.48 (s, 3H), 1.79 (s, 3H), 1.66 (s, 3H), 1.45 (s, 9H), 0.54 (d, J=17.10, 9H). $^{13}$C (125 MHz, $CDCl_3$) δ 177.7, 171.2, 151.1, 142.6, 137.9, 137.8, 137.3, 134.3, 134.2, 132.9, 131.2, 130.4, 129.4, 129.2, 129.1, 128.5, 128.4, 128.2, 126.5, 125.8, 125.7, 125.4, 125.2, 124.9, 121.0, 120.9, 60.4, 46.7, 41.3, 34.0, 28.3, 24.1, 24.1, 21.1, 20.2, 20.0, 14.2

4: To a stirring solution of 2 (2.0 g, 3.40 mmol) in methanol (1 mL) at room temperature, sodium hydroxide (5.5 mL, 1M in water, 5.5 mmol) was charged. Then, the solution was heated to 50° C. for 1.5 h. The reaction was quenched with 2M HCl, adjusting pH to 7. After quenching the reaction was concentrated under vacuum, DCM (30 mL) was added, organic layer separated, and then the aqueous layer was extracted with DCM (10 mL×5). Organic layers were combined, dried with $Na_2SO_4$, concentrated, recrystallized from cold DCM to obtain intermediate 4 74% yield.

$^1$H NMR (500 MHz, $CDCl_3$) δ 7.90 (d, J=9.05, 1H), 7.69 (d, J=8.65, 1H), 7.49-7.51 (m, 2H), 7.41-7.44 (m, 2H), 7.28-7.34 (m, 3H), 7.09 (d, J=7.25, 2H), 6.88-6.91 (m, 2H), 4.40 (d, J=18.05, 1H), 3.54-3.64 (m, 2H), 2.46 (s, 3H), 1.78 (s, 3H), 1.67 (s, 3H), 0.47 (d, J=15.95, 9H). $^{31}$P (202 MHz, $CDCl_3$) δ65.29

A round bottom was charged with phosphine oxide 4, (1.11 g, 2.20 mmol), $Pd_2dba_3$ (0.051 g, 0.055 mmol), RuPHOS (0.103 g, 0.22 mmol), and sodium t-butoxide (0.253 g, 2.64 mmol). Then the flask was treated for vacuum-purged with argon 3 times. Phenyl bromide (0.28 mL, 0.2.64 mmol), and THF (7 mL) were added. The reaction mixture was stirred at rt for 5 minutes and heated at 67° C. for 6 h before analyzed by LC-MS. The reaction mixture was passed through a pad of celite and washed with THF (3×2 mL). The crude was concentrated and purified by column chromatography by silica gel using 0 to 70% ethylacetate to hexane to obtain intermediate 6 (57% yield). MS of the product −580

A septa capped vial was purged with argon and then charged with 6 (0.021 g, 0.036 mmol) and THF maintaining inert atmosphere. Then the vial was cooled to −78° C. Then $Me_2SO_4$ (0.0043 g, 0.180 mmol) and LDA (0.036 mL, 0.072 mmol) were added. It was stirred at −78° C. for 2 h before it was warmed to rt, stirred for another 1 h. Then quenched with 2M HCl (0.2 mL). The product was purified from flash chromatography (EtOAc to hexane, 0 to 70%) to obtain intermediate 8 in 40% yield. $^{31}$P (202 MHz, $CDCl_3$) δ 60.43

The phosphine oxide 2 (0.150 g, 0.255 mmol) was charged to a 50 mL 3-nekced rb with magnetic stir-bar. A reflux condenser was added, and the closed atmosphere was purged with Ar using vacuum-purge cycles. Toluene (5.0 mL) (sparged with argon before use) was charged followed by triethylamine (0.142 mL, 1.02 mmol) and $HSiCl_3$ (0.077 mL, 0.765 mmol). The mixture was then immersed in an oil bath and left for stirring at 65° C. for 3 h. The reaction was monitored by $^{31}$P NMR from crude mixture. The reaction was then cooled to rt and quenched with 6 mL of degassed (Ar sparge) 15% NaOH at 0° C. The mixture was left for stirring at rt for 30 mins. The aqueous layer was then separated and extracted under $N_2$ with EtOAc (3×5 mL). The combined organics were dried with $Na_2SO_4$. The solution passed through a narrow neutral alumina (0.5") and eluted with 50% EtOAc in DCM. Then the solvent was pumped off to yield the product Iv (81%).

$^1$H NMR (500 MHz, $CDCl_3$) δ 8.32 (d, J=8.20, 1H), 7.87 (d, 8.70, 1H), 7.74 (d, J=8.70), 7.58-7.61 (m, 1H), 7.48-7.52 (m, 1H), 7.27-7.39 (m, 5H), 7.12 (s, 1H), 7.09 (s, 1H), 4.41 (dd, J=13.15, 2.35, 1H), 4.05 (dd, J=22.36, 13.10, 1H), 2.46 (s, 3H), 1.83 (s, 3H), 1.65 (s, 3H), 1.48 (s, 9H), 0.42 (d, J=12.20, 9H). $^{31}$P (202 MHz, $CDCl_3$) δ −12.26

Ligands Iu and Ix were prepared by the same procedure ising intermediates 4 and 8 respectively.

Analytical data (Iu): $^{31}$P (202 MHz, $CDCl_3$) δ 7.60
Analytical data (Ix): $^{31}$P (202 MHz, $CDCl_3$) δ 7.32

Example 14: Pd-Catalyzed Asymmetric Alkene Aryloxyarylation Using Ligand Ix

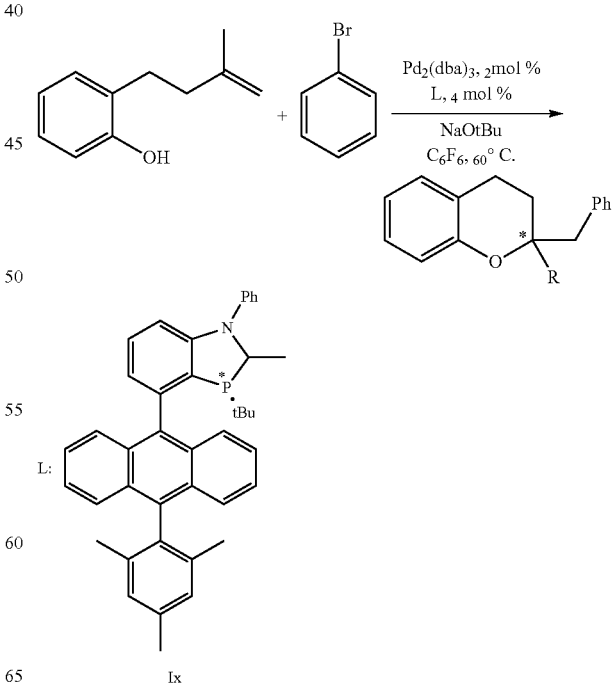

A vial was charged with Pd2(dba)3 (2.0 mg, 0.002 mmol, 2 mol % complex, 4 mol % Pd), Ligand Ix (2.3 mg, 0.004 mmol, 4 mol %), NaOt-Bu (19.0 mg, 0.2 mmol, 2.0 equiv.), the phenol substrate (16.2 mg, 1.0 equiv.), the bromobenzene (0.022 mL, 0.2 mmol, 2.0 equiv.), and $C_6F_6$ (0.5 mL) in a $N_2$ filled glove box. The mixture was stirred under nitrogen at 60° C. for 12 h before being analyzed by GC-MS. ee condition: Chiral column condition: Chiralcel OJ-3, n-heptane/1-propanol, 99.5/0.5 isocratic, 25° C., 1.5 mL/min. 100% conversion, 66% ee. MS of the product—238, 147, 91.

Example 15: Suzuki Coupling Using Ligand Ic

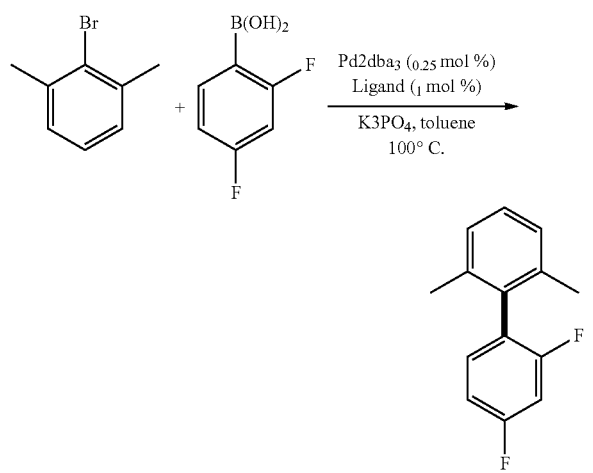

A mixture of 2,6-dimethylbromobenzene (1.0 g), 2,4 difluorophenylboronic acid (1.019 g), $Pd_2(dba)_3$ (0.0124 g), Ligand Ic C (22 mg) and $K_3PO_4$ (3.44 g) in toluene (11 mL) was heated at 100° C. overnight. Full conversion was observed.

1H NMR (400 MHz, CDCl3) δ 7.22-7.18 (m, 1H), 7.13-7.08 (m, 3H), 6.98-6.89 (m, 2H), 2.05 (s, 6H);

Example 16: Suzuki Coupling with Ligands Ic, Id, If, Ig

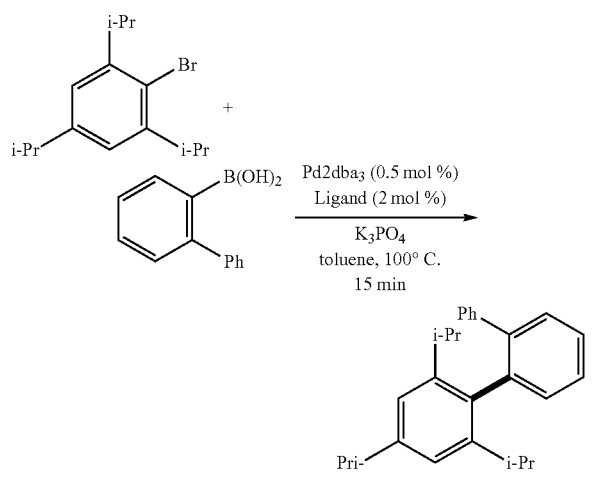

A mixture of 2,4,6-tri-iso-propyl-1-bromobenzene (141 mg, 0.500 mmol), 2-biphenyl boronic acid (149 mg, 0.75 mmol), $Pd_2(dba)_3$ (2.3 mg, 0.0025 mmol), Ligand Ic, Id, If, or Ig (2 mol %, 0.010 mmol), and $K_3PO_4$ (318 mg, 1.50 mmol) in toluene (1.0 mL) was heated at 100° C. for 15 min. Full conversion to the desired product was observed with all ligands.

1H NMR (400 MHz, CDCl$_3$) δ 7.51 (dd, J=7.7, 1.2 Hz), 7.44 (dt, J=7.2, 1.4 Hz, 1H), 7.37 (dt, J=7.4, 1.5 Hz, 1H), 7.24 (dd, J=7.5, 1.1 Hz, 1H), 7.07-7.15 (m, 5H), 6.92 (s, 2H), 2.88 (sept, J=6.8 Hz, 1H), 2.56 (sept, J=6.8 Hz, 2H), 1.26 (d, J=6.8 Hz, 6H), 1.03 (d, J=6.8 Hz, 6H), 0.86 (d, J=6.8 Hz, 6H).

Example 17: Asymmetric Hydrogenation Using Ligand Ii

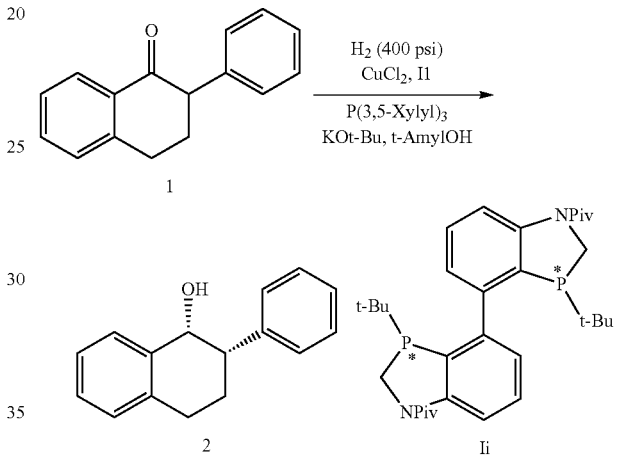

To a mixture of $CuCl_2$ (0.7 mg, 0.005 mmol), ligand Ii (2.8 mg, 0.005 mmol), tris(3,5-dimethylphenyl)phosphine (2.2 mg, 0.005 mmol), and KOt-Bu (5.6 mg, 0.05 mmol) were added 2-phenyl-1-tetralone (22 mg, 0.1 mmol) and t-AmylOH (0.25 mL) under nitrogen. The reaction vessel was transferred into an autoclave and pressurized with hydrogen to 400 psi. The reaction mixture was stirred at this pressure and 20° C. for 24 h. After release of the hydrogen and purging with nitrogen, the reaction mixture was filtered through a plug of diatomaceous earth to afford crude alcohol 2 (>95% conversion, 97:3 er). The enantiomeric excess of the products was determined by chiral HPLC with a Phenomenex Lux Cellulose 3 (4.6×150 mm) column (heptane/denatured ethanol=95:5, 1.5 mL/min, 10° C., $rt_1$ (enantiomer 1, minor)=10.3 min, $rt_2$ (enantiomer 2, major)=17.1 min. MS calcd for $C_{17}H_{17}O_2^+$ [M-18]$^+$: 207.3, found 207.2.

Example 18: Asymmetric Hydrogenation Using Ligand IIa

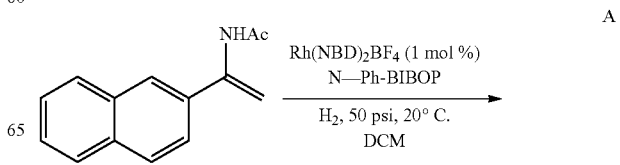

41
-continued

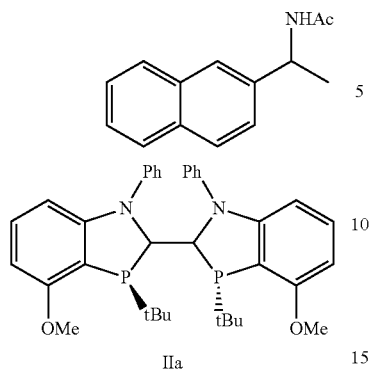

IIa

To a glass vial were added 1.0 mg Rh(NBD)₂(BF₄) (0.0027 mmol) and 2.4 mg (0.004 mmol) ligand IIa and 1 mL degassed CH₂Cl₂. The mixture was stirred under nitrogen for 10 min. Then 57 mg N-(1-naphthalenyl)vinylacetamide (0.27 mmol) was added to the mixture. The vial was inserted into a hydrogenation reactor. The reactor was then sealed, purged with N₂ three times and H₂ three times. The mixture was stirred under 50 psi H₂ pressure at 20° C. for 20 h. Upon completion, the reactor was vented and a sample was taken and analyzed. The desired product N-(1-(naphthalenyl)ethyl)acetamide was observed as [$C_{14}H_{15}NO+H^+$]=214.1, and 95.2:4.8 er; Enantioselectivity was determined on HPLC using a ChiralPak AD-3 column, 150 mm×4.6 mm, heptane/n-propanol 90:10, 1.3 mL/min, 30° C., $t_1$=4.41 min, $t_2$=5.72 min.

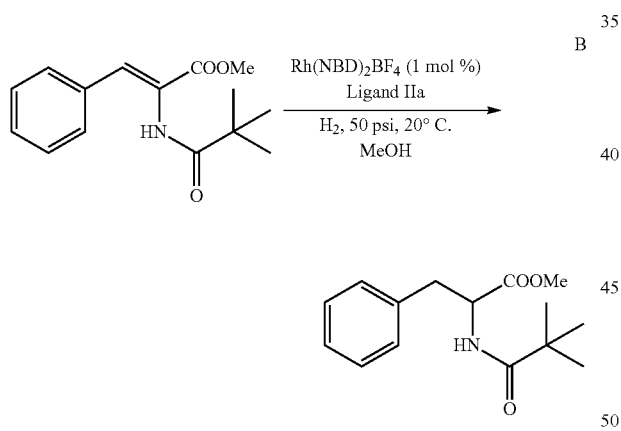

To a glass vial were added 0.95 mg Rh(NBD)₂(BF₄) (0.0025 mmol) and 2.24 mg (0.0038 mmol) ligand IIa and 1 mL degassed MeOH. The mixture was stirred under nitrogen for 10 min. Then 65.3 mg methyl (Z)-3-phenyl-2-pivalamidoacrylate (0.25 mmol) was added to the mixture. The vial was inserted into a hydrogenation reactr. The reactor was then sealed, purged with N₂ three times and H₂ three times. The mixture was stirred under 50 psi H₂ pressure at 20° C. for 20 h. Upon completion, the reactor was vented and a sample was taken and analyzed. The desired product methyl pivaloylphenylalaninate was observed as [$C_{15}H_{22}NO_3+H^+$]=264.1 and 95.0:5.0 er; Enantioselectivity was determined on HPLC using a Kromasil 3-Amycoat column, 250 mm×4.6 mm, heptane/EtOH 95:5, 1.3 mL/min, 25° C., $t_1$=6.05 min, $t_2$=6.92 min.

42
Example 19: Synthesis of Ligand IIa

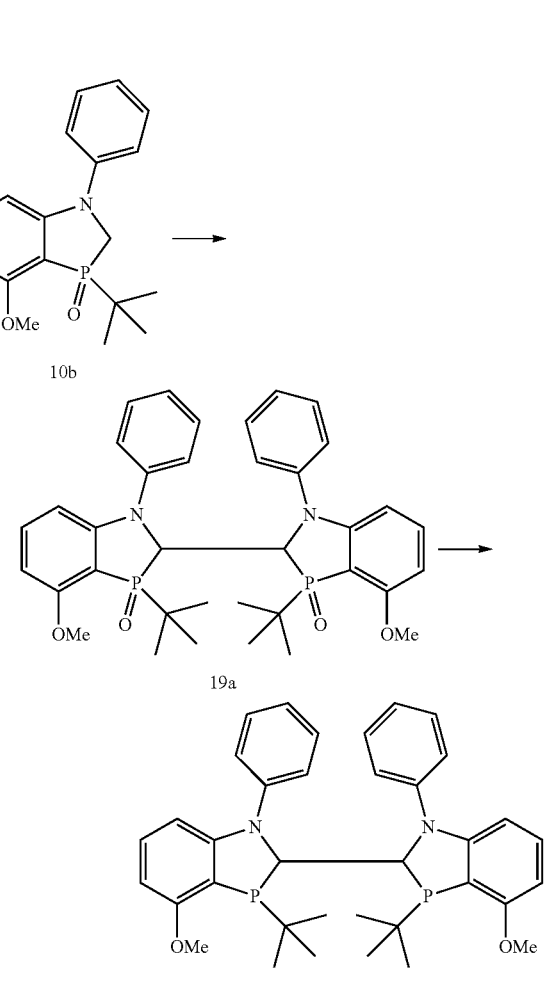

A solution containing 3-(tert-butyl)-4-methoxy-1-phenyl-1,2-dihydrobenzo[d][1,3]azaphosphole 3-oxide (10b) (0.500 g, 1.59 mmol) in THF (10 mL, degassed with argon) was cooled to −65° C. LDA (1M in THF/hexanes, 2.38 mL, 2.38 mmol) was added dropwise. After addition, the reaction mixture was stirred between −70 to −65° C. for 1 h. Cu(OAc)₂ (1.152 g, 6.35 mmol) was added and stirred at −65° C. for 10 minutes. The reaction was then slowly warmed to room temperature. The reaction was then quenched with NH₄OH solution (10 mL) and water (10 mL) and stirred for 10 minutes. The solution was then extracted with CH₂Cl₂ (3×10 mL). The organic layers were combined, washed with water (10 mL), dried (MgSO₄) and concentrated. The crude was then purified by column chromatography on silica gel using 0 to 5% MeOH in CH₂Cl₂ as eluent to afford 19a as a yellow solid. ¹H (400 MHz, CDCl₃) δ=7.05-6.99 (m, 10H), 6.88-6.83 (m, 2H), 6.29 (dd, J=8.12, 4.12 Hz, 2H), 6.23 (dd, J=8.28, 2.68 Hz, 2h), 5.30-5.18 (m, 1H), 3.84 (s, 6H), 1.24 (d, J=16.12 Hz, 18H). ¹³C NMR (100 MHz, CDCl₃)=162.4, 153.4, 153.3, 143.5, 135.1, 129.6, 128.8, 123.2, 128.8, 106.4, 106.38, 106.3, 103.4, 102.6, 102.0, 102.0, 101.9, 55.3, 25.5, 25.5, 51.9, 51.9, 34.9, 34.2, 24.5. ³¹P (162 MHz, CDCl₃) δ=65.13. HRMS (ESI+/TOF): m/z calcd for $C_{36}H_{43}N_2O_4P_2^+$ [M+H]⁺ 629.2693, found 629.2691. Optical rotation: $[\alpha]_D^{18}$=+181.66 (c=0.01, MeOH).

An oven dried 50 mL Schlenk flask equipped with a magnetic stir bar was charged with phosphine oxide 19a (100 mg, 0.159 mmol) and m-xylene (5 mL). The solution was thoroughly degassed by vacuum purge-and-refill with argon before addition of 330 uL Et$_3$N (2.39 mmol) and 160 uL HSiCl$_3$ (1.59 mmol). The resulting mixture was heated to 145° C. for 14 h. A sample was taken and $^{31}$P NMR analysis indicated complete conversion to the free phosphine. The mixture was cooled down to 0° C. with an ice bath and quenched with degassed 30% aqueous NaOH (5 mL) over 10 min. The resulting mixture was then stirred at 60° C. for 1 h. The mixture was cooled to room temperature and the layers were separated under argon. The aqueous layer was washed once with degassed MTBE. The combined organic was dried over MgSO$_4$ and concentrated. It was purified on a short neutral alumina column with degassed EtOAc as eluent. The major fraction was collected and dried to yield the product IIa as an off white solid (30 mg, 40% yield). $^1$H NMR (400 MHz, CDCl$_3$) δ 7.16 (m, 2H), 7.12 (m, 4H), 7.03-6.98 (m, 4H), 6.81-6.75 (m, 2H), 6.68 (d, J=7.9 Hz, 2H), 6.40 (d, J=7.9 Hz, 2H), 4.17 (J=5.6 Hz, 2H), 3.79 (s, 6H), 0.84 (d, J=12.4 Hz, 18H); $^{31}$P (162 MHz, CDCl$_3$) δ −6.88;

What is claimed is:

1. A compound of formula I

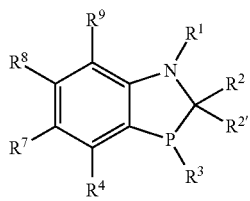

I wherein each

R$^1$ is selected from H, C$_{1-6}$alkyl, —C(O)C$_{1-6}$alkyl, —C(O)NHR$^5$, —SO$_2$C$_{1-6}$alkyl, —S(O)C$_{1-6}$alkyl, —P(O)R$^{13}$R$^{14}$, —SiR$^{13}$, —C(=NR$^{13}$)NR$^{13}$R$^{14}$, optionally substituted benzyl and optionally substituted aryl or heteroaryl;

R$^2$ and R$^{2'}$ are each independently selected from the group consisting of hydrogen, halo, perhaloalkyl, —NR$^{11}$R$^{12}$, —OR$^{11}$, —SR$^{11}$, —Si(R$^{11}$)$_3$, P(O)R$^{13}$R$^{14}$, —CN, —NO$_2$, —OH, alkyl, alkenyl, alkynyl, cycloalkyl, heterocycloalkyl, arylalkyl, heteroarylalkyl, bicycloaryl, heterobicycloaryl, C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, benzyl, aryl and heteroaryl are unsubstituted or substituted;

R$^3$ is selected from alkyl, cycloalkyl or optionally substituted aryl;

R$^4$ is hydrogen, halo, perhaloalkyl, —NR$^{11}$R$^{12}$, —OR$^{11}$, —SR$^{11}$, —Si(R$^{11}$)$_3$, —CN, —NO$_2$, —OH, alkyl, alkenyl, alkynyl, cycloalkyl, heterocycloalkyl, benzyl, aryl, alkyl, heteroarylalkyl, bicycloaryl, heterobicycloaryl, C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, aryl and heteroaryl are unsubstituted or substituted; or R$^4$ is X—R$^6$; or R$^4$ is the group

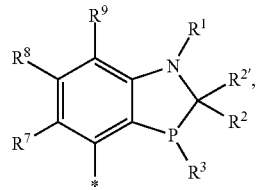

wherein * indicates the point of attachment;

X is selected from O, NR$^{10}$, CR$^{11}$R$^{12}$ and S;

R$^5$ is selected from C$_{1-6}$alkyl and optionally substituted phenyl each R$^6$, R$^7$, R$^8$ and R$^9$ is independently selected from the group consisting of hydrogen, halo, perhaloalkyl, —NR$^{11}$R$^{12}$, —OR$^{11}$, —SR$^{11}$, —Si(R$^{11}$)$_3$, —CN, —NO$_2$, —OH, alkyl, alkenyl, alkynyl, cycloalkyl, heterocycloalkyl, benzyl, aryl, alkyl, heteroarylalkyl, heterobicycloaryl, —C(O)alkyl, —C(S)alkyl, —S(O)$_{1-2}$alkyl, benzyl, aryl, heteroaryl, aryloxy and heteroaryloxy, wherein each alkyl, alkenyl, alkynyl, cycloalkyl, heterocycloalkyl, aryl and heteroaryl are unsubstituted or substituted;

R$^{10}$, R$^{11}$ and R$^{12}$ are independently selected from H, C$_{1-6}$alkyl, C$_{1-6}$alkenyl, C$_{1-6}$alkynyl, perhaloC$_{1-6}$alkyl, —C(O)C$_{1-6}$alkyl, cycloalkyl, heterocyclyl, optionally substituted benzyl, optionally substituted aryl and optionally substituted heteroaryl; and R$^{13}$ and R$^{14}$ are independently selected from C$_{1-6}$alkyl and optionally substituted aryl;

and the diastereomers and enantiomers thereof.

2. The compound according to claim 1 wherein

R$^1$ is selected from H, C$_{1-6}$alkyl, —C(O)C$_{1-6}$alkyl, —C(O)NHR$^5$, —SO$_2$C$_{1-6}$alkyl, optionally substituted benzyl and optionally substituted aryl;

R$^2$ and R$^{2'}$ are independently selected from H, C$_{1-6}$alkyl, C$_{3-6}$cycloalkyl, CH$_2$C$_{3-10}$cycloalkyl, —C(O)C$_{1-6}$alkyl, optionally substituted aryl, heteroaryl or CH$_2$-aryl and —P(O)R$^8$R$^9$;

R$^3$ is selected from is selected from C$_{1-6}$alkyl, C$_{3-6}$cycloalkyl and optionally substituted aryl;

R$^4$ is selected from optionally substituted aryl and —X—R$^6$; or

R$^4$ is the group

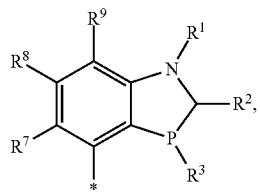

wherein * indicates the point of attachment;

X is selected from a O, —NR$^{10}$ and S;

R$^5$ is selected from C$_{1-6}$alkyl and optionally substituted phenyl

R$^6$ is selected from C$_{1-6}$alkyl, C$_{3-6}$cycloalkyl, optionally substituted aryl and optionally substituted heteroaryl;

R$^7$, R$^8$ and R$^9$ are each H;

R$^{10}$ is selected from H, C$_{1-6}$alkyl, C$_{3-6}$cycloalkyl, optionally substituted aryl and optionally substituted heteroaryl;

$R^{13}$ and $R^{14}$ are independently selected from $C_{1-6}$alkyl and optionally substituted aryl;
and the diastereomers and enantiomers thereof.

3. The compound according to claim 1 wherein
$R^1$ is selected from H, —$C_{1-3}$alkyl, —C(O)—$C_{1-4}$alkyl, —C(O)NHR$^5$, benzyl, and phenyl, optionally substituted with one to two groups selected from —CF$_3$, —OC$_{1-3}$alkyl, halogen, —NH(C$_{1-3}$alkyl), and —N(C$_{1-3}$alkyl)$_2$;
$R^2$ is selected from H, $C_{1-3}$alkyl, —CH$_2$-adamantyl, phenyl, pyridyl, -benzyl and —CH$_2$naphthyl, wherein the phenyl, pyridyl, -benzyl and —CH$_2$naphthyl is optionally substituted with one to three groups selected from $C_{1-3}$alkyl, —OCH$_3$ —CF$_3$ and halogen;
$R^{2'}$ is H or if $R^2$ is $C_{1-6}$alkyl, $R^{2'}$ may be $C_{1-6}$alkyl; or
$R^3$ is $C_{1-6}$alkyl;
$R^4$ is selected from phenyl, optionally substituted with one to three groups selected from —OCH$_3$, —CF$_3$, $C_{1-3}$alkyl and halogen; or
$R^4$ is —X—R$^6$; or
$R^4$ is selected from

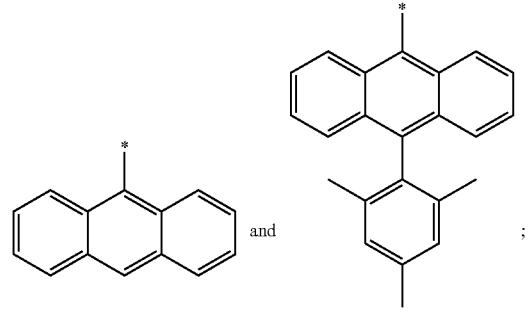 [SMILES: *c1c2ccccc2cc2ccccc12 ; *c1c2ccccc2c(-c2c(C)cc(C)cc2C)c2ccccc12]

or
$R^4$ is the group

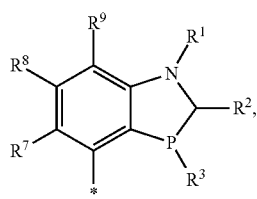

wherein * indicates the point of attachment;
X is O;
$R^5$ is phenyl, optionally substituted with one to three groups selected from —OCH$_3$, —CF$_3$, $C_{1-3}$alkyl and halogen;
$R^6$ is $C_{1-3}$alkyl; and
$R^7$, $R^8$ and $R^9$ are each H;
and the diastereomers and enantiomers thereof.

4. The compound according to claim 1 wherein
$R^1$ is selected from H, —CH$_3$, —C(O)-t-butyl, —C(O)NHR$^5$, benzyl, and phenyl, optionally substituted with —CF$_3$ or —OCH$_3$;
$R^2$ is selected from H, $C_{1-3}$alkyl, —CH$_2$-adamantyl, 2,4,6-triisopropylbenzyl, —CH$_2$naphthyl and pyridyl optionally substituted with —OCH$_3$;
$R^{2'}$ is H or if $R^2$ is methyl, $R^{2'}$ may be methyl;
$R^3$ is t-butyl;
$R^4$ is 2,6-dimethoxyphenyl,

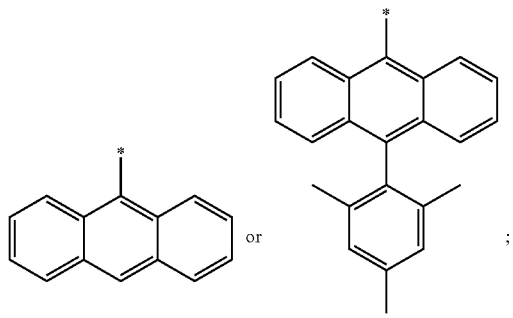 [SMILES: *c1c2ccccc2cc2ccccc12 ; *c1c2ccccc2c(-c2c(C)cc(C)cc2C)c2ccccc12]

or
$R^4$ is the group

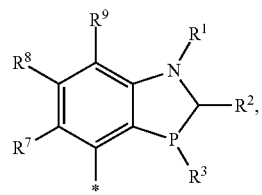

wherein * indicates the point of attachment; or
$R^4$ is —X—R$^6$;
X is O; and
$R^6$ is methyl;
$R^5$ is phenyl; and
$R^7$, $R^8$ and $R^9$ are each H;
and the diastereomers and enantiomers thereof.

5. A compound selected from the group consisting of

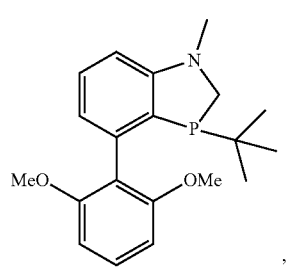

Ia

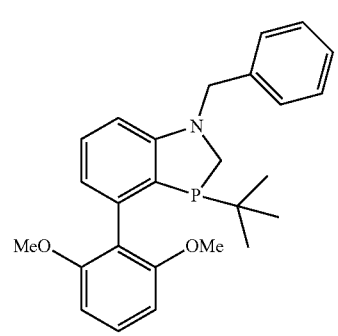

Ib

Ic
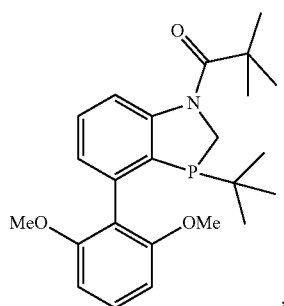
,
Id
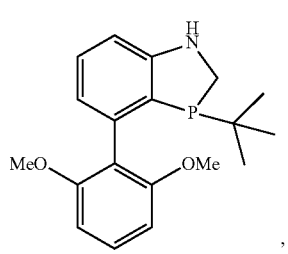
,
Ie
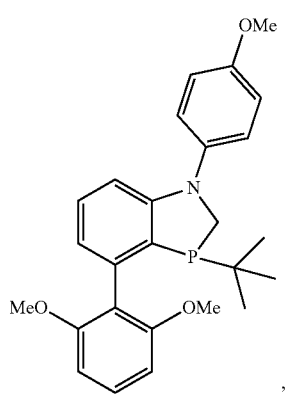
,
If
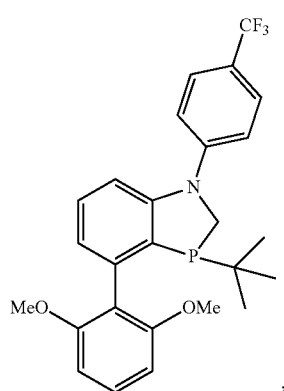
,
Ig
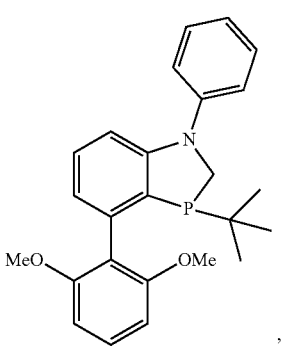
,
Ih
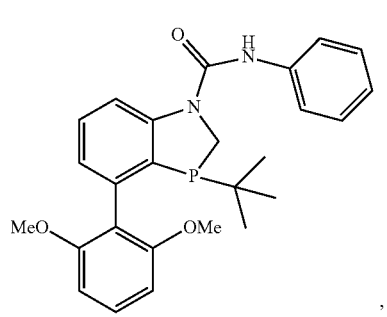
,
Ii
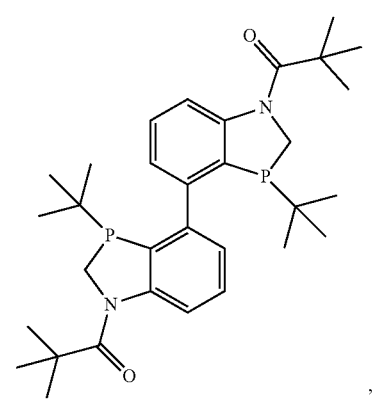
,
Ij
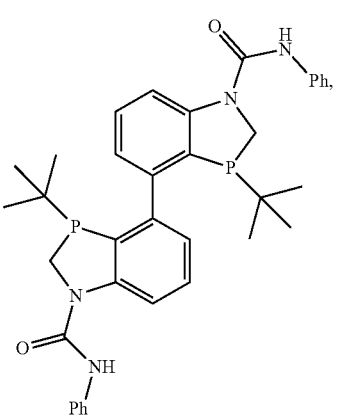

Ik
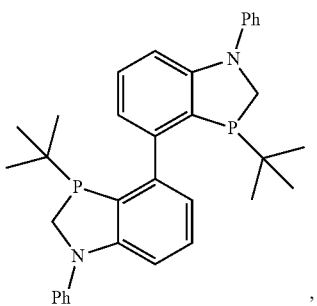
Il
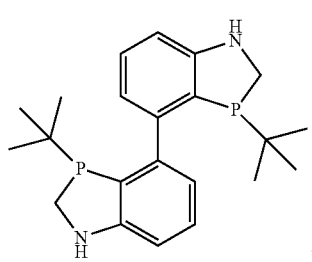
Im
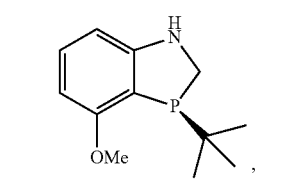
In
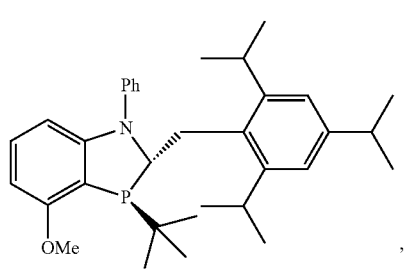
Io
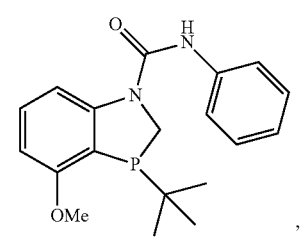
Ip
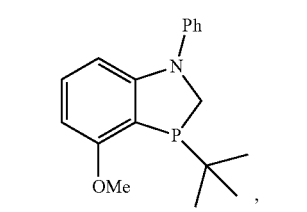
Iq
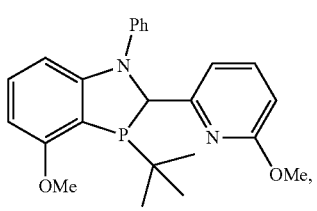
Ir
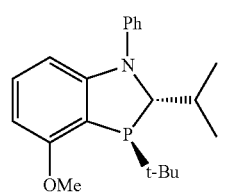
Is
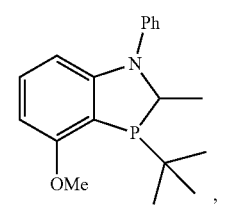
It
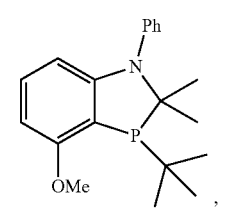
Iu
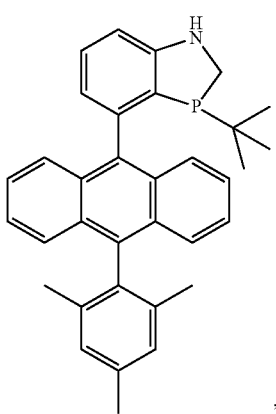

Iv
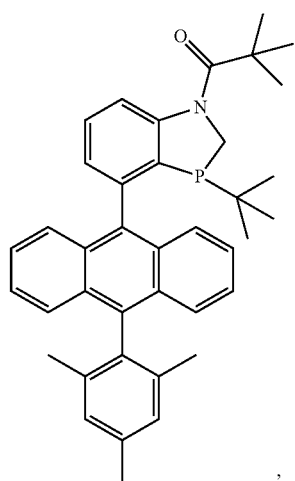
Iw
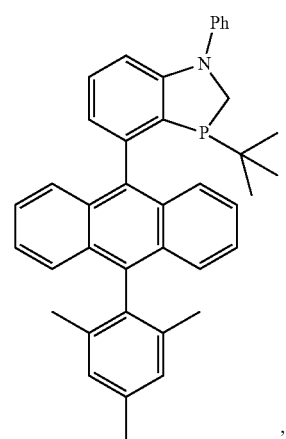
Ix
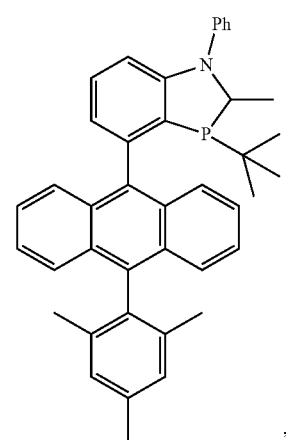
Iy
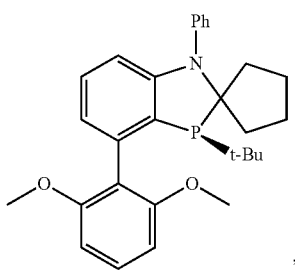
Iz
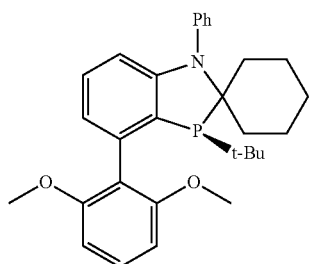
Iaa
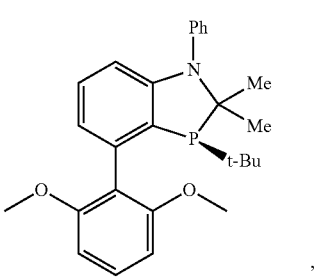
Ibb
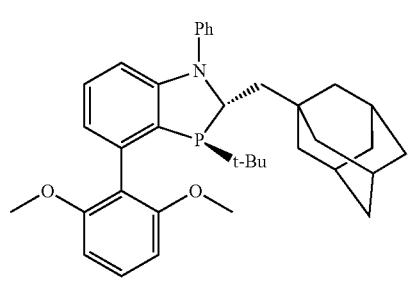
Icc
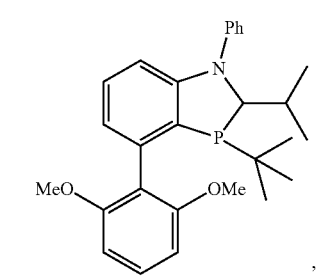
Idd
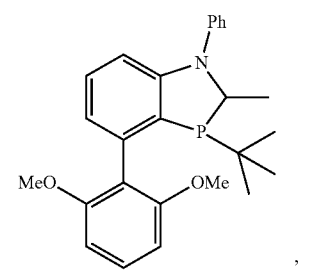

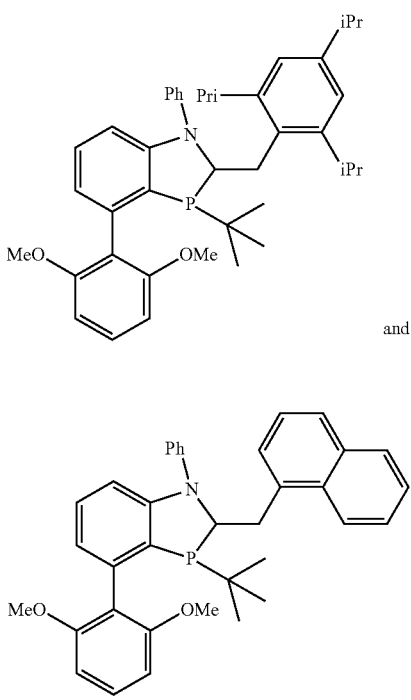

and

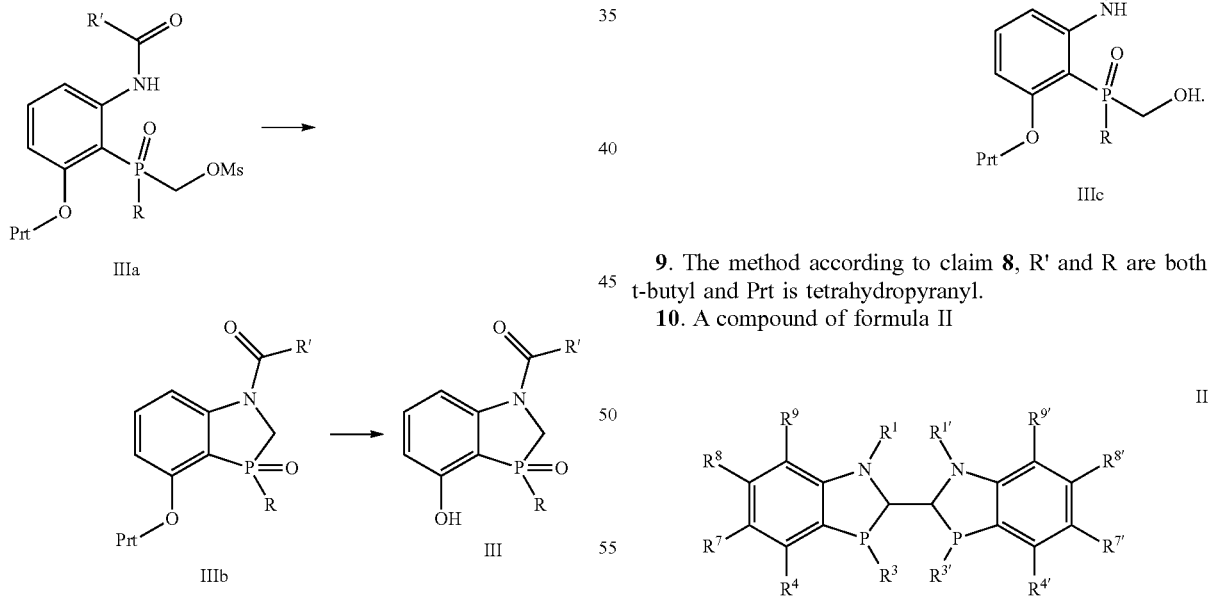

and the enantiomers and diastereomers thereof.

6. A method for the synthesis of compound III comprising

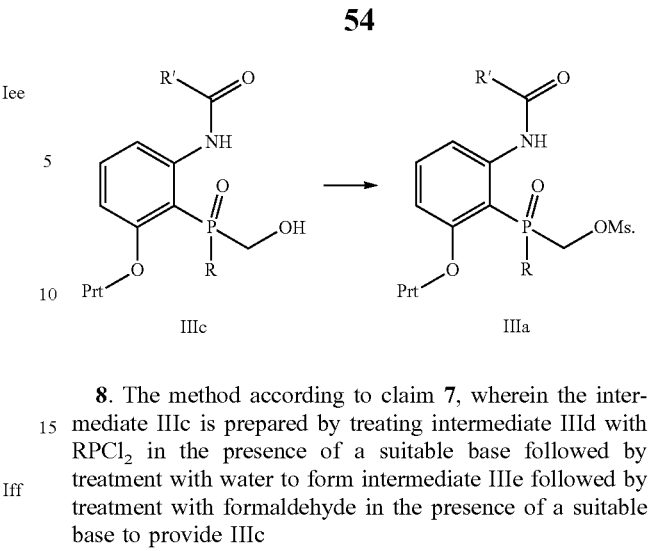

reacting intermediate IIIa, wherein R' and R are independently selected from $C_{1-6}$alkyl and Prt is a protecting group with a suitable base to provide intermediate IIIb; and removing the protecting group to provide III.

7. The method according to claim 6 wherein the intermediate IIIa is prepared by treating intermediate IIIc with methanesulfonyl chloride in the presence of a suitable base

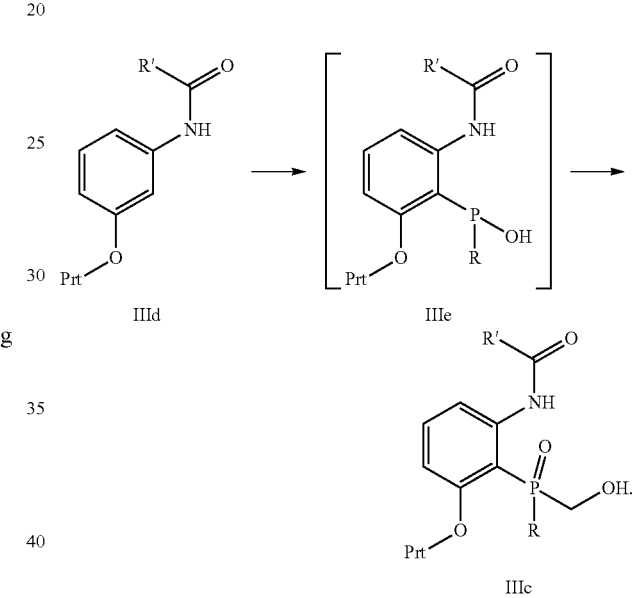

8. The method according to claim 7, wherein the intermediate IIIc is prepared by treating intermediate IIId with $RPCl_2$ in the presence of a suitable base followed by treatment with water to form intermediate IIIe followed by treatment with formaldehyde in the presence of a suitable base to provide IIIc

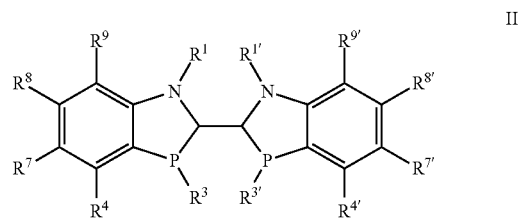

9. The method according to claim 8, R' and R are both t-butyl and Prt is tetrahydropyranyl.

10. A compound of formula II wherein $R^1$ and $R^{1'}$ are independently selected from —$SO_2$aryl, —C(O)-aryl, —C(O)$C_{1-6}$alkyl, —NC(O)-aryl and —NC(O)$C_{1-6}$alkyl, wherein each aryl and alkyl is optionally substituted;

$R^3$ and $R^{3'}$ are independently selected from alkyl, cycloalkyl and optionally substituted aryl;

$R^4$, $R^{4'}$, $R^7$, $R^{7'}$, $R^8$, $R^{8'}$, $R^9$ and $R^{9'}$ are independently selected from hydrogen, halo, perhaloalkyl, —$NR^{11}R^{12}$, —$OR^{11}$, —$SR^{11}$, —$Si(R^{11})_3$, —CN, —$NO_2$, —OH, alkyl, alkenyl, alkynyl, cycloalkyl, heterocycloalkyl, benzyl, aryl, alkyl, heteroarylalkyl, bicycloaryl, heterobicycloaryl, —C(O)alkyl, —C(S)alkyl, —$S(O)_{1-2}$alkyl, benzyl, aryl, heteroaryl, aryloxy and heteroaryloxy, wherein each alkyl, alkenyl, alkynyl, cycloalkyl, heterocycloalkyl, aryl and heteroaryl are unsubstituted or substituted; and $R^{11}$ and $R^{12}$ are independently selected from H, $C_{1-6}$alkyl, $C_{3-6}$cycloalkyl, $CH_2C_{3-10}$cycloalkyl, —$C(O)C_{1-6}$alkyl, optionally substituted aryl, heteroaryl and —$CH_2$-aryl; and and the diastereomers and enantiomers thereof.

* * * * *